US011452823B2

(12) United States Patent
Toddywala et al.

(10) Patent No.: US 11,452,823 B2
(45) Date of Patent: Sep. 27, 2022

(54) BREATH-ENHANCED JET NEBULIZER

(71) Applicants: INSPIRX, INC., Durham, NC (US); THE RESEARCH FOUNDATION FOR THE STATE UNIVERSITY OF NEW YORK, Albany, NY (US)

(72) Inventors: Rohinton D. Toddywala, Princeton, NJ (US); Vijay Shukla, Highland Park, NJ (US); Gerald C. Smaldone, Setauket, NY (US)

(73) Assignees: INSPIRX, INC., Durham, NY (US); THE RESEARCH FOUNDATION FOR THE STATE UNIVERSITY OF NEW YORK, Albany, NY (US)

( * ) Notice: Subject to any disclaimer, the term of this patent is extended or adjusted under 35 U.S.C. 154(b) by 452 days.

(21) Appl. No.: 16/328,939

(22) PCT Filed: Sep. 1, 2017

(86) PCT No.: PCT/US2017/049812
§ 371 (c)(1),
(2) Date: Feb. 27, 2019

(87) PCT Pub. No.: WO2018/045263
PCT Pub. Date: Mar. 8, 2018

(65) Prior Publication Data
US 2019/0192790 A1    Jun. 27, 2019

Related U.S. Application Data

(60) Provisional application No. 62/382,985, filed on Sep. 2, 2016.

(51) Int. Cl.
*A61M 11/00*    (2006.01)
*A61M 11/06*    (2006.01)
*A61M 15/00*    (2006.01)

(52) U.S. Cl.
CPC ......... *A61M 11/002* (2014.02); *A61M 11/003* (2014.02); *A61M 11/06* (2013.01);
(Continued)

(58) Field of Classification Search
CPC .............. A61M 11/002; A61M 11/003; A61M 11/06; A61M 15/0013; A61M 15/0015;
(Continued)

(56) References Cited

U.S. PATENT DOCUMENTS 2,772,117 A * 11/1956 Ritzau .................... B05B 5/025
239/135
3,658,059 A *  4/1972 Steil ..................... A61M 11/002
128/200.21
(Continued)

FOREIGN PATENT DOCUMENTS

EP          3551261 A1    10/2019
WO    WO 99/11310 A1     3/1999
(Continued)

OTHER PUBLICATIONS

Official Action dated Apr. 9, 2020, received from the European Patent Office.
(Continued)

*Primary Examiner* — Kathryn E Ditmer
(74) *Attorney, Agent, or Firm* — Jonathan D. Ball; Greenberg Traurig, LLP

(57) ABSTRACT

A breath-enhanced jet nebulizer is configured with a low liquid retention reservoir and a narrow liquid delivery passage to efficiently and efficiently aerosolize small drug volumes with minimal waste. Aerosol particles are directed through aerosol passage for delivery, although larger liquid particles are directed away from the aerosol outlet and recycled to the liquid reservoir.

28 Claims, 31 Drawing Sheets

(52) U.S. Cl.
CPC .... *A61M 15/0015* (2014.02); *A61M 15/0016* (2014.02); *A61M 15/0018* (2014.02); *A61M 15/0021* (2014.02); *A61M 2205/183* (2013.01); *A61M 2205/44* (2013.01); *A61M 2205/581* (2013.01); *A61M 2206/14* (2013.01)

(58) Field of Classification Search
CPC .......... A61M 15/0016; A61M 15/0018; A61M 2205/581; A61M 2206/14; B05B 17/06
See application file for complete search history.

(56) References Cited

U.S. PATENT DOCUMENTS

| | | | | |
|---|---|---|---|---|
| 3,861,386 | A * | 1/1975 | Harris | B05B 17/0615 239/338 |
| 4,116,387 | A * | 9/1978 | Kremer, Jr. | B05B 7/0012 261/78.2 |
| 4,456,179 | A * | 6/1984 | Kremer | A61M 11/06 239/338 |
| RE33,642 | E * | 7/1991 | Lester | B05B 7/0012 128/200.21 |
| 5,054,477 | A * | 10/1991 | Terada | A61M 16/125 128/200.14 |
| 5,241,954 | A * | 9/1993 | Glenn | A61M 11/06 128/200.18 |
| 5,522,380 | A * | 6/1996 | Dwork | A61M 15/0086 128/200.23 |
| 5,544,647 | A | 8/1996 | Jewett et al. | |
| 5,549,102 | A * | 8/1996 | Lintl | A61M 11/002 128/203.25 |
| 5,875,774 | A * | 3/1999 | Clementi | B05B 7/2435 128/200.18 |
| 5,957,389 | A * | 9/1999 | Wunderlich | A61M 11/06 239/338 |
| 6,044,841 | A * | 4/2000 | Verdun | A61M 11/06 128/200.18 |
| 6,116,233 | A * | 9/2000 | Denyer | A61M 11/06 128/200.18 |
| 6,338,443 | B1 * | 1/2002 | Piper | A61M 11/06 128/200.18 |
| 6,631,721 | B1 * | 10/2003 | Salter | A61M 11/06 128/203.21 |
| 6,929,003 | B2 | 8/2005 | Blacker et al. | |
| 7,234,459 | B2 * | 6/2007 | Del Bon | A61M 11/06 128/200.14 |
| 7,878,194 | B2 * | 2/2011 | Hamaguchi | A61M 15/0021 128/200.21 |
| 8,286,629 | B2 * | 10/2012 | Esaki | A61M 11/06 128/200.21 |
| 8,464,715 | B2 * | 6/2013 | Flynn, Sr. | A61M 16/0816 128/205.24 |
| 8,596,263 | B2 * | 12/2013 | Piper | A61M 16/20 128/200.18 |
| 8,973,572 | B2 * | 3/2015 | Chen | A61M 15/0018 128/200.23 |
| 2004/0031485 | A1 * | 2/2004 | Rustad | A61M 11/06 128/200.18 |
| 2005/0051161 | A1 * | 3/2005 | Anandampillai | A61M 15/0088 128/200.23 |
| 2007/0193577 | A1 * | 8/2007 | Keller | A61K 9/0078 128/200.14 |
| 2007/0227535 | A1 * | 10/2007 | Harrington | A61M 15/0096 128/200.21 |
| 2010/0095958 | A1 * | 4/2010 | King | A61M 11/001 128/200.18 |
| 2012/0318261 | A1 * | 12/2012 | Newhouse | A61M 15/0018 128/200.23 |
| 2013/0327323 | A1 * | 12/2013 | Rubin | A61M 16/1055 128/200.18 |
| 2014/0116427 | A1 * | 5/2014 | Pevler | A61M 11/02 128/200.18 |
| 2016/0022933 | A1 * | 1/2016 | Ciancone | A61M 15/0086 128/200.23 |
| 2016/0228656 | A1 * | 8/2016 | Vasandani | A61M 15/0018 |
| 2017/0368273 | A1 * | 12/2017 | Rubin | A61M 11/005 |
| 2018/0008789 | A1 * | 1/2018 | Alizoti | A61M 16/209 |

FOREIGN PATENT DOCUMENTS

| | | |
|---|---|---|
| WO | WO 2012/026963 A2 | 3/2012 |
| WO | WO 2012/0338861 A1 | 3/2012 |
| WO | WO 2012/069531 A2 | 5/2012 |
| WO | WO 2014/085719 A1 | 6/2014 |

OTHER PUBLICATIONS

International Search Report dated Nov. 30, 2017 issued in PCT/US2017/049812.

* cited by examiner

| RUN | MMAD | RH% | Time [min] | Vol [mL] | Output | RM | Residual | Total Recovery |
|---|---|---|---|---|---|---|---|---|
| 1 | 1.41 | 24% | 15 | 1 | 35.8 | 28.0 | 67.1 | 102.9 |
| 2 | 1.46 | 45% | 15 | 1 | 42.3 | 31.4 | 54.8 | 97.2 |
| 3 | 1.45 | 45% | 15 | 1 | 39.5 | 30.1 | 59.2 | 98.7 |
| 4 | 1.77 | 24% | 22 | 2 | 72.8 | 44.8 | 28.6 | 101.3 |
| 5 | 1.50 | 31% | 22 | 2 | 70.3 | 46.3 | 27.1 | 97.4 |
| 6 | 1.94 | 31% | 22 | 2 | 73.2 | 40.5 | 29.7 | 102.9 |

Fig. 11

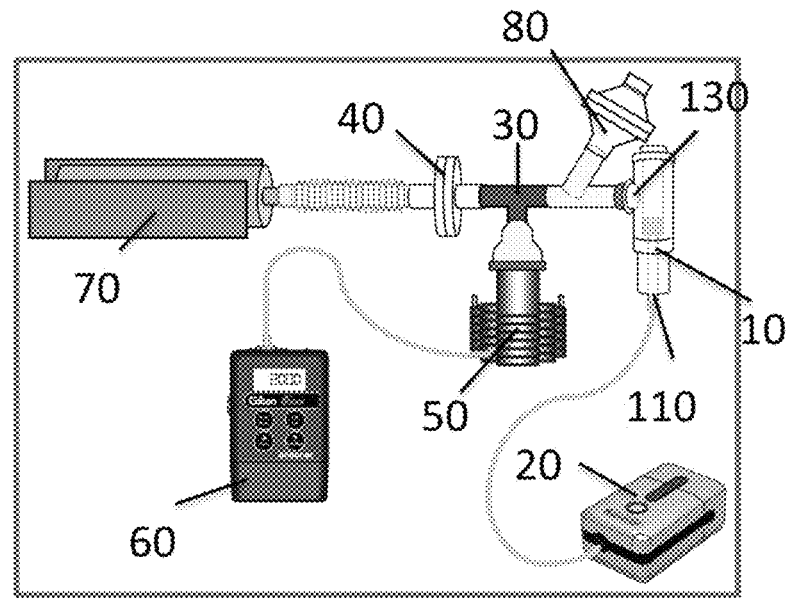
Fig. 12A Experimental Set-up Using Filtered Mouthpiece
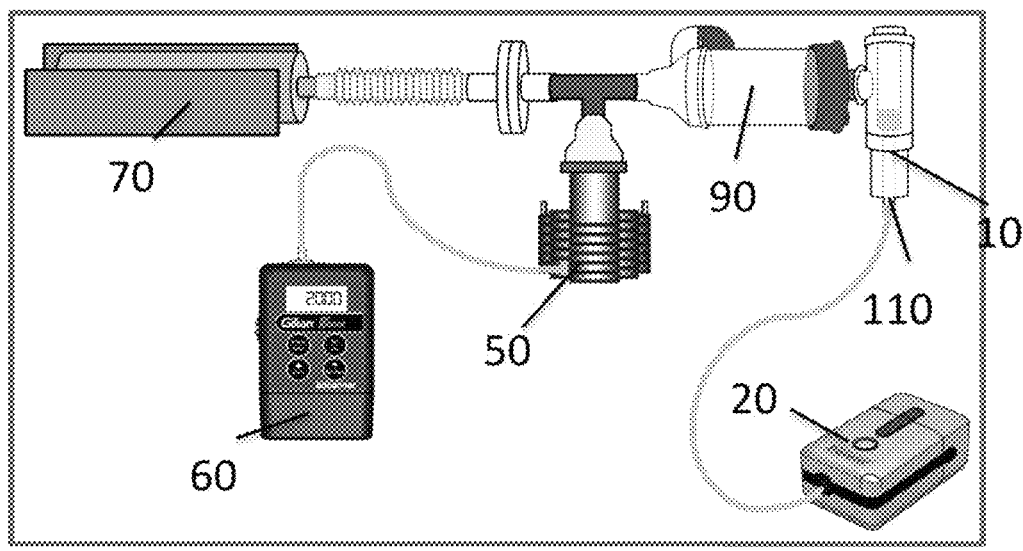
Fig. 12B Experimental Set-up Using Valved Holding Chamber

| RUN | MMAD | RH% | Time [min] | Vol [mL] | IM | RM | Residual | VHC | LEAK | Recovery |
|---|---|---|---|---|---|---|---|---|---|---|
| 21 | 1.13 | 26% | 15 | 1 | 33.8 | 30.9 | 52.2 | | 9.2 | 95.3 |
| 86 | 1.09 | 45% | 15 | 1 | 25.1 | 23.7 | 66.1 | | 6.0 | 97.3 |
| 101 | 1.28 | 40% | 15 | 1 | 24.0 | 20.9 | 64.8 | | 6.6 | 95.3 |
| 104 | 1.28 | 52% | 15 | 1 | 26.8 | 23.5 | 55.9 | | 10.8 | 96.8 |
| 87 | 1.25 | 45% | 22 | 2 | 40.5 | 35.9 | 38.7 | | 18.1 | 97.3 |
| 88 | 1.23 | 48% | 22 | 2 | 42.5 | 37.3 | 37.9 | | 15.9 | 96.4 |
| 46 | 1.13 | 35% | 17 | 1 | 32.5 | 30.2 | 39.4 | 5.0 | | 76.8 |
| 85 | 1.06 | 45% | 15 | 1 | 25.9 | 24.9 | 55.5 | 1.0 | | 82.4 |
| 103 | 1.17 | 52% | 15 | 1 | 29.0 | 28.7 | 51.8 | 0.9 | | 81.5 |
| 64 | 1.23 | 34% | 15 | 2 | 39.7 | 35.5 | 30.4 | 1.9 | | 72.0 |
| 84 | 1.15 | 48% | 22 | 2 | 27.6 | 27.5 | 53.1 | 1.0 | | 81.9 |
| 102 | 1.27 | 50% | 22 | 2 | 38.3 | 35.1 | 38.6 | 2.3 | | 79.2 |

| RUN | MMAD | RH% | Time [min] | Vol [mL] | IM | RM | Residual | VHC | LEAK | Recovery |
|---|---|---|---|---|---|---|---|---|---|---|
| 7 | 1.16 | 21% | 15 | 1 | 45.0 | 37.8 | 51.1 | | 5.1 | 101.2 |
| 11 | 1.15 | 31% | 13 | 1 | 43.1 | 36.3 | 51.9 | | 4.7 | 99.7 |
| 97 | — | 40% | 15 | 1 | 48.0 | — | 48 | | 2.5 | 99.9 |
| 98 | — | 42% | 15 | 1 | 50.8 | — | 42.3 | | 3.7 | 96.8 |
| 74 | 1.74 | 44% | 22 | 2 | 62.9 | 49.9 | 32.7 | | 5.6 | 101.1 |
| 75 | 1.37 | 55% | 22 | 2 | 62.2 | 49.1 | 32.8 | | 4.6 | 99.6 |
| 47 | 1.05 | 35% | 17 | 1 | 34.5 | 32.6 | 45.3 | 0.4 | | 80.2 |
| 89 | 1.14 | 48% | 15 | 1 | 34.6 | 32.3 | 56.4 | 0.8 | | 91.8 |
| 96 | — | 40% | 15 | 1 | 33.3 | — | 45.3 | 1.0 | | 79.6 |
| 99 | — | 42% | 15 | 1 | 40.4 | — | 48.6 | 2.1 | | 91.1 |
| 71 | 1.24 | 33% | 22 | 2 | 66.6 | 57.3 | 29.5 | 2.3 | | 98.4 |
| 72 | 1.34 | 45% | 22 | 2 | 61.1 | 51.3 | 28.2 | 2.1 | | 91.3 |
| 73 | 1.33 | 45% | 22 | 2 | 54.5 | 47.6 | 36.2 | 2.0 | | 92.7 |
| 90 | 1.22 | 55% | 22 | 2 | 52.8 | 47.1 | 36.2 | 2.2 | | 91.1 |
| 91 | 1.17 | 42% | 15 | 2 | 57.1 | 51.6 | 38.2 | 1.8 | | 97.2 |
| 92 | 1.23 | 42% | 15 | 2 | 60.3 | 52.7 | 32.8 | 1.8 | | 95.1 |
| 93 | 1.22 | 34% | 15 | 2 | 60.8 | 55.3 | 32.6 | 1.9 | | 95.2 |

(A)
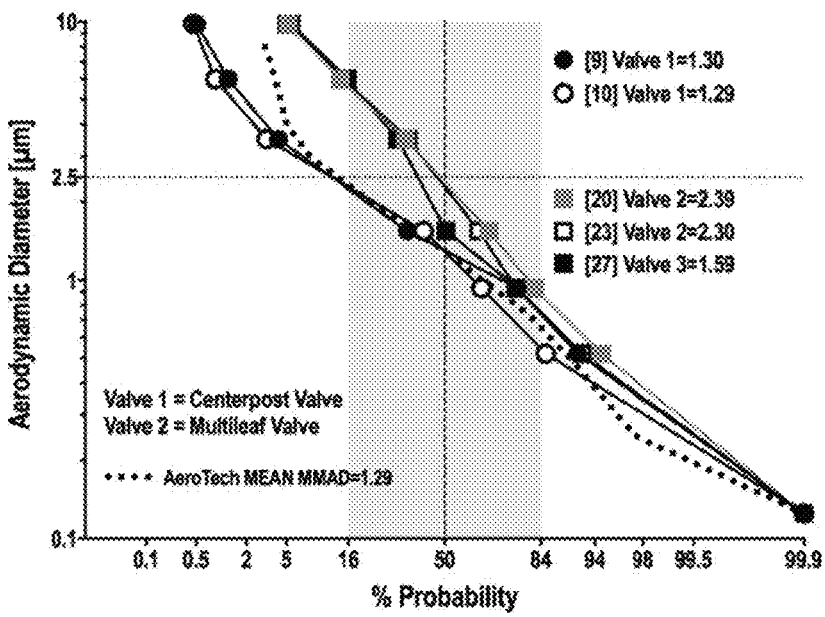

(B)

| Valve | BP | MODE | Run | Solution | Air Flow | [LPM] | MMAD | RH% | Run Time [min] | Vol [mL] | IM | RF | RM | Residual | LEAK | Tubing | Recovery |
|---|---|---|---|---|---|---|---|---|---|---|---|---|---|---|---|---|---|
| 1 | Standing Cloud | Continuous | 9 | IFN Control | Traveler | 3.8 | 1.30 | <25 | 4+15 | 2 | 44.3 | 0.88 | 39.0 | 32.7 | — | 21.3 | 98.3 |
| 1 | Standing Cloud | Continuous | 10 | IFN Control | Traveler | 3.8 | 1.29 | <25 | 3+15 | 2 | 47.2 | 0.88 | 41.6 | 30.8 | — | 19.7 | 97.6 |
| 2 | Standing Cloud | Continuous | 20 | IFN Control | Traveler | 3.8 | 2.39 | <25 | 3+15 | 2 | 62.8 | 0.51 | 31.8 | 32.1 | — | 0.7 | 95.6 |
| 2 | Standing Cloud | Continuous | 23 | IFN Control | Traveler | 3.8 | 2.30 | <25 | 3+15 | 2 | 42.6 | 0.51 | 21.7 | 54.8 | — | 4.2 | 101.6 |
| 2 | Standing Cloud | Continuous | 27 | IFN Control | Traveler | 3.8 | 1.59 | <25 | 3+15 | 2 | 48.3 | 0.68 | 29.4 | 42.3 | — | 11.8 | 103.4 |

(C)
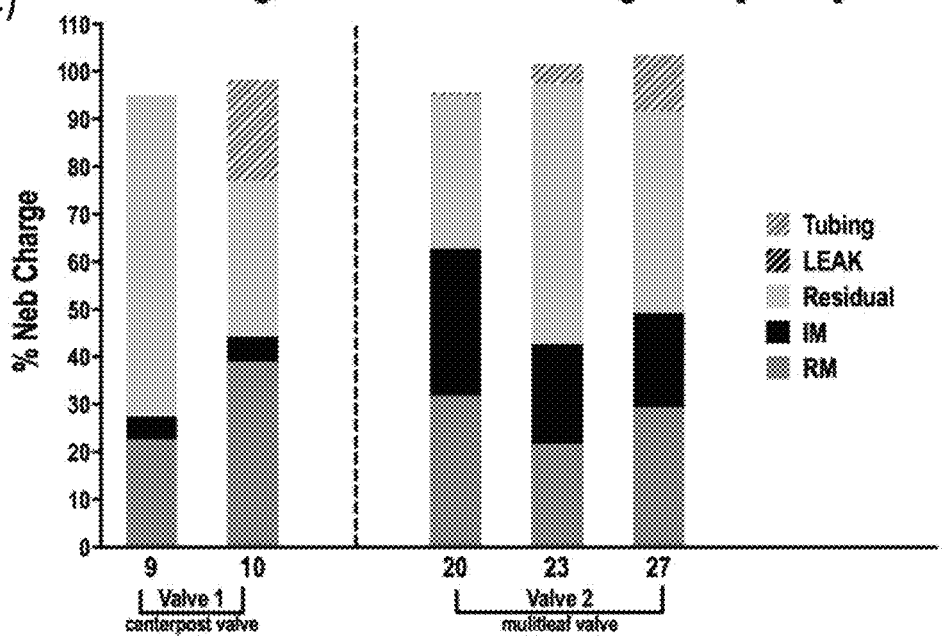

Fig. 30

(A)
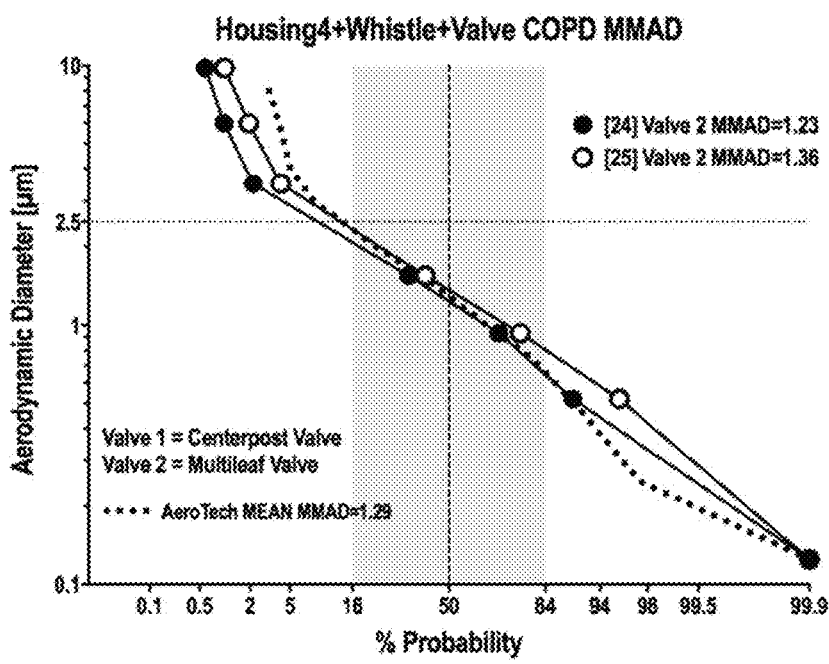
(B)
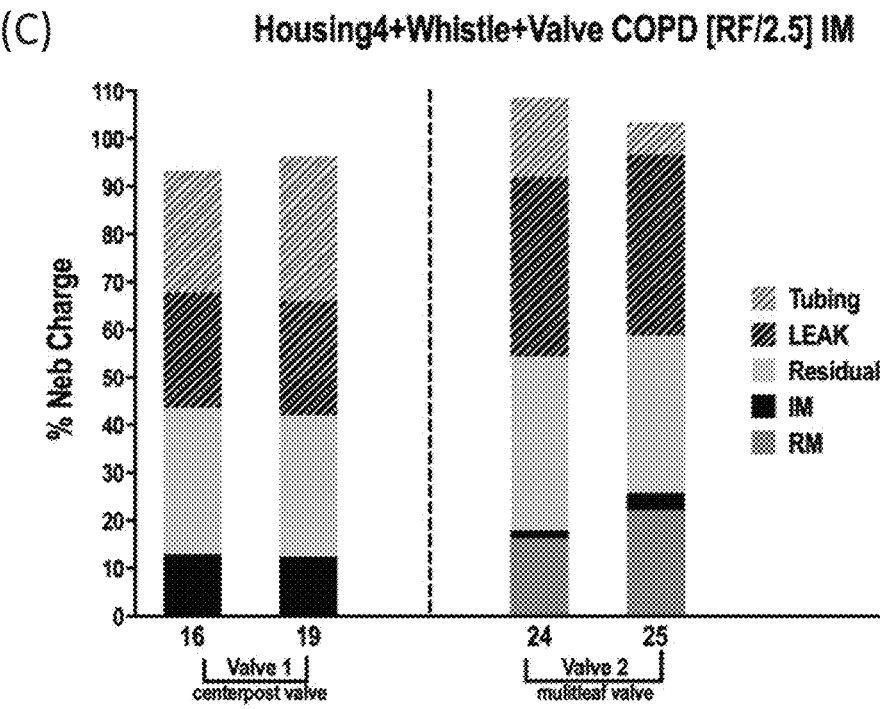
Fig. 31

BREATH-ENHANCED JET NEBULIZER

CROSS-REFERENCE TO RELATED APPLICATIONS

The present application is a '371 of PCT Application Number PCT/US2017/049812, filed on Sep. 1, 2017, which is claiming benefit of U.S. Provisional Application No. 62/382,985, which was filed on Sep. 2, 2016, the contents of both of which are incorporated by reference.

BACKGROUND

The present application relates generally to an apparatus for generating an aerosol, and more specifically to a jet nebulizer for aerosolizing and dispensing a small volume of a liquid drug or medicament.

Nebulizers convert solutions or liquid suspensions of a drug or medicament to a fine spray or aerosol that can be inhaled by a patient. Nebulized or aerosolized solutions are commonly used for respiratory delivery of medication, which can treat a variety of conditions and diseases. When fragmented into small drops, liquid medicaments can be more efficiently incorporated into and adsorbed by the lungs.

In order to administer an effective dose of medication, many commercially-available nebulizers require a relatively large starting volume of liquid due to the various system inefficiencies associated with both the generation and delivery of the aerosol. For instance, in many commercial systems, as much as 50% or more of the starting liquid volume remains in the nebulizer, with typically less than 20%, such as 5-10%, of the starting liquid volume effectively delivered to the patient. Notwithstanding the availability of a variety of nebulizer designs, efficient generation and delivery of medicated aerosols are desired in order to provide effective patient treatment while minimizing waste and reducing costs.

SUMMARY

Disclosed is a breath-enhanced jet nebulizer configured to aerosolize small drug volumes and deliver size-specific aerosol particles, while recycling larger aerosol particles in the nebulizer that would not be effectively reach the alveolar region of the lungs. The recycled liquid can be re-aerosolized to form smaller particles for delivery to the lungs. As described in detail herein, the jet nebulizer comprises a minimal number of parts, which facilitates easy disassembly, cleaning, and re-assembly thereof.

In accordance with embodiments of the present application, an apparatus for forming an aerosol comprises a main housing, a flue disposed within an inner volume of the main housing, and a cap comprising a one-way valve sealably engaged with the main housing. The inner volume of the main housing may be substantially cylindrical shape. A one-way valve is incorporated into the cap.

An axially-oriented gas inlet nozzle is integral with the main housing and includes a gas orifice at an upper distal end. An annular fluid reservoir is disposed between an outer wall of the gas inlet nozzle and a sloped inner wall of the main housing.

The flue includes a sleeve portion that is slideably engaged with the gas inlet nozzle to define an annular liquid flow passage. Also, an annular aerosol passage is disposed between an outer wall of the flue and an inner wall of the main housing.

A primary baffle is axially aligned with and spaced apart from the gas orifice, and one or more secondary baffles extend from an outer surface of the flue into the aerosol passage.

In an embodiment, the aforesaid apparatus comprises a mouthpiece that is in fluid communication with an aerosol outlet extending through a sidewall of the main housing. In another embodiment, this apparatus comprises an inhalation orifice provided between and in fluid communication with the mouthpiece and the aerosol outlet of the apparatus, and the inhalation orifice opening valve is configured to adjust the size of the aerosol particles passing through the inhalation orifice opening valve. In an embodiment, the inhalation opening valve has one or more central openings, and in another embodiment, the inhalation opening valve has one or more side openings.

In an another embodiment, the apparatus comprises an audible indicator provided to the cap of the apparatus, such that said audible indicator is provided upstream of the one-way valve and configured to restrict inlet air flow, thereby facilitating slow and deep breathing of the user.

In another embodiment, the apparatus comprises both the audible indicator and the orifice opening valve, wherein the opening valve has either one or more central openings or one or more side openings.

The apparatus can be used to form an aerosol. An example method includes adding an initial volume of 2 ml or less of a liquid drug or medicament to the liquid reservoir, and flowing pressurized gas through the gas inlet nozzle at a flow rate of 1 to 10 liters per minute to form aerosol particles from the liquid volume.

BRIEF DESCRIPTION OF SEVERAL VIEWS OF THE DRAWINGS

The following detailed description of specific embodiments of the present application can be best understood when read in conjunction with the following drawings, where like structure is indicated with like reference numerals and in which:

FIG. 11 is a table summarizing the aerodynamic diameter data and liquid volume recovery data from FIGS. 9 and 10;

FIG. 12A is a schematic diagram of an experimental setup used to produce ventilated aerosols using a filtered mouthpiece according to various embodiments;

FIG. 12B is a schematic diagram of an experimental setup used to produce ventilated aerosols using a valved holding chamber according to various embodiments;

FIG. 15 is a table summarizing the aerodynamic diameter data and liquid volume recovery data from FIGS. 13 and 14;

FIG. 18 is a table summarizing the aerodynamic diameter data and liquid volume recovery data from FIGS. 16 and 17;

FIG. 25 is a flow diagram of the jet nebulizer illustrating the motion of aerosol particles and gases during inhalation; and FIG. 26 is a flow diagram for the jet nebulizer illustrating the motion of aerosol particles and gases during exhalation.

FIG. 29A is a plot showing the distribution of aerosol aerodynamic diameter. FIG. 29B is a table summarizing the aerodynamic diameter data and liquid volume recovery data; and FIG. 29C bar graph showing the % Neb Charge with respect to runs 11-13 and 18, 21, 22 and 26.

FIG. 30 provides data using the set-up of FIG. 12A using the nebulizer of the present invention having a centerpost valve or multileaf valve and whistle using the interferon placebo formulation in solution containing surfactant labeled with $^{99m}Tc$ using a breathing profile consistent with slow and deep breathing from runs 9 and 10 using a nebulizer of the present invention with one centerpost valve and whistle and runs 20, 23 and 27 using a nebulizer of the present invention with multi-leaf valve and whistle. FIG. 30A is a plot showing the distribution of aerosol aerodynamic diameter. FIG. 30B is a table summarizing the aerodynamic diameter data and liquid volume recovery data; and FIG. 30C bar graph showing the % Neb Charge.

FIG. 31 provides data using the set-up of FIG. 12A using the nebulizer of the present invention having a centerpost valve or multileaf valve and whistle using the interferon placebo formulation in solution containing surfactant labeled with $^{99m}Tc$ using a breathing profile consistent with COPD breathing from runs 16 and 19 using a nebulizer of the present invention with one centerpost valve and whistle and runs 24 and 25 using a nebulizer of the present invention with multi-leaf valve and whistle. FIG. 31A is a plot showing the distribution of aerosol aerodynamic diameter. FIG. 31B is a table summarizing the aerodynamic diameter data and liquid volume recovery data; and FIG. 31C bar graph showing the % Neb Charge.

DETAILED DESCRIPTION

Figure 1:
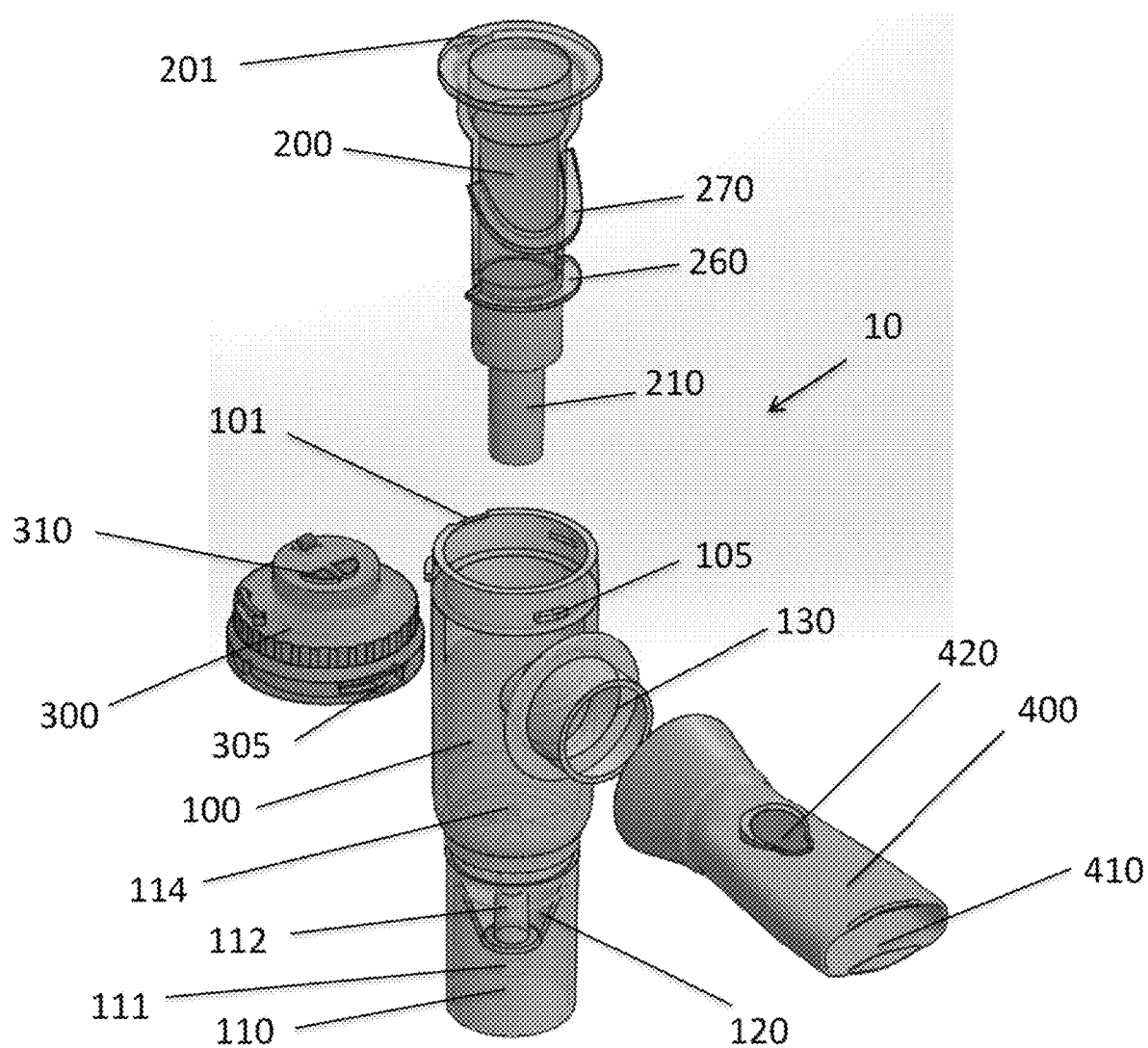
FIG. 1 is an exploded perspective view of a jet nebulizer according to various embodiments.

Reference will now be made in greater detail to various embodiments of the subject matter of the present application, some embodiments of which are illustrated in the accompanying drawings. The same reference numerals will be used throughout the drawings to refer to the same or similar parts.

Disclosed is a breath-enhanced jet nebulizer. In various embodiments, the jet nebulizer is configured to efficiently aerosolize relatively small drug volumes. In contrast to many commercial nebulizers that require 3-6 ml or more of liquid in order to have sufficient material to aerosolize and deliver an effective dose to a patient, the presently-disclosed jet nebulizer is adapted to operate with a starting liquid volume of 0.5-2 ml, although smaller or larger volumes can be used.

An exploded perspective view of an example breath-enhanced jet nebulizer is shown in FIG. 1. Nebulizer 10 includes a main housing 100 having a substantially cylindrical construction. A substantially cylindrical flue 200 comprising a sleeve 210 and one or more secondary baffles 260, 270 is configured to be inserted within the main housing 100. During use, a top cap 300, which is secured to the main housing 100, holds the flue 200 within the housing 100 at a predetermined alignment. The top cap 300 may be secured to the housing 100 by cooperative engagement of cap threads or cap notches 305 with corresponding threads or tabs 105 on the housing.

In embodiments, a mouthpiece 400 is attached to the nebulizer 10 to deliver aerosol particles to a patient. For instance, mouthpiece 400 may be attached to the nebulizer 10 by a friction fit. Mouthpiece 400 includes an opening 410 and an exhalation valve 420. The exhalation valve 420 is configured to open when a patient exhales into the mouthpiece 400 via opening 410 and thereby exhaust the exhalation from the patient, and close when a patient inhales through the mouthpiece. Thus, exhalation valve 420 allows discharge of respiratory air during exhalation while inhibiting an inflow of ambient air during inhalation. Main housing 100, flue 200, top cap 300 and mouthpiece 400 may be constructed of a polymer material and may be formed, for example, by casting, extrusion, or molding such as 3D blow molding.

For example, one or more of the components of the nebulizer 10 can be formed from a polymer material such as thermoset and elastomeric monomers and polymers, and monomeric and polymeric thermoplastics including fluorocarbons, polyesters, polyamides, nylon, polybutadienes, polyvinyl chloride, silicone resins, polypropylene, as well as combinations and composites thereof.

The main housing 100 includes a compressed gas inlet 110, a liquid reservoir 120, and an aerosol outlet 130. The aerosol outlet 130 is formed in a lateral sidewall of the main housing 100. The compressed gas inlet 110 comprises a tubular gas passage 111 that extends through a gas inlet nozzle 112, which terminates at an upper distal end in a gas orifice 114. In embodiments, gas and liquid are mixed together by passing a quickly-moving gas stream through the gas orifice.

Figure 2:
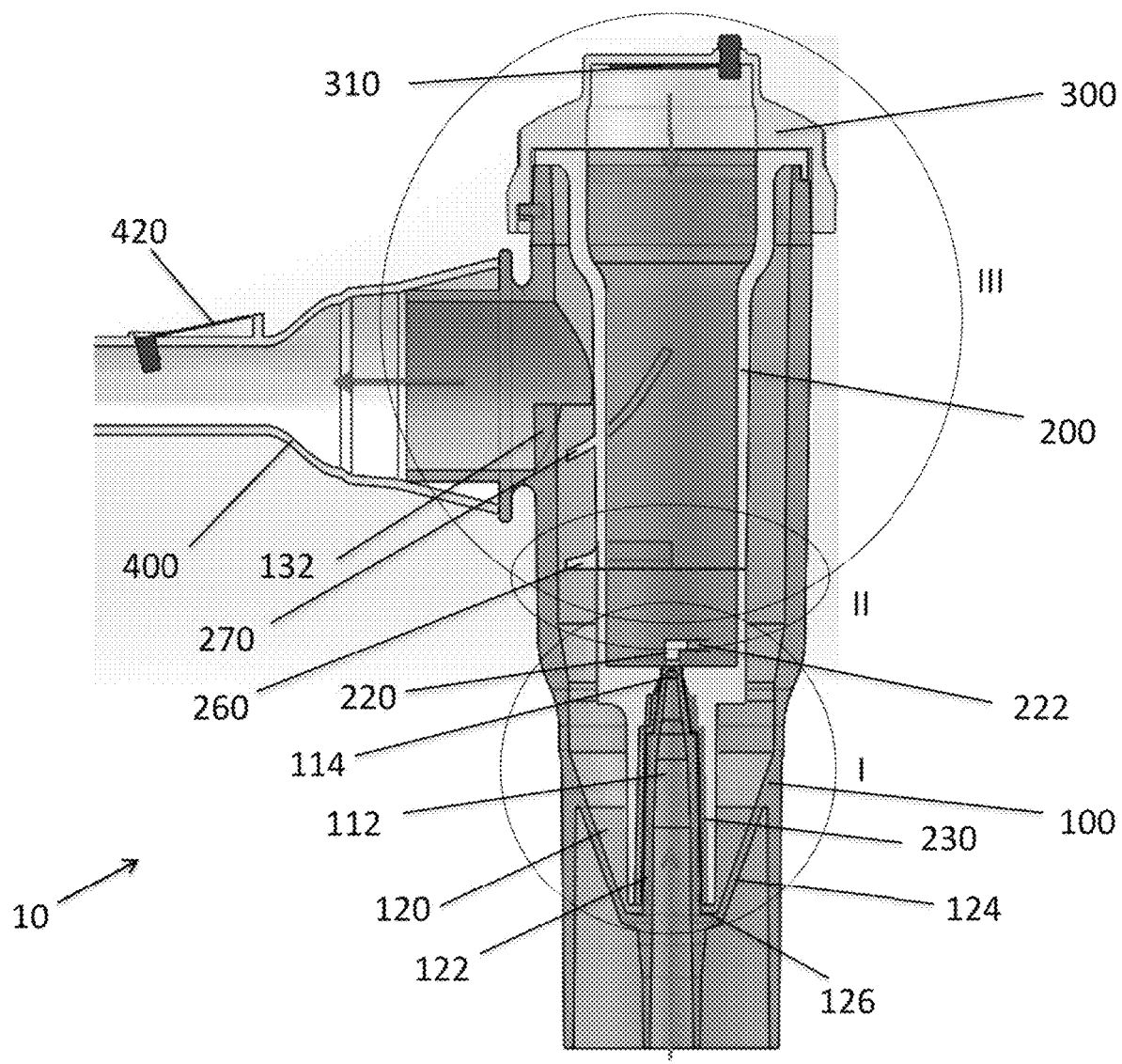
FIG. 2 is a cross-sectional view of an assembled jet nebulizer including a housing, a flue disposed within the housing and secured by a top cap, and a mouthpiece attached to an aerosol outlet of the housing.

Gas orifice 114 is sized to provide a sonic gas jet as pressurized gas flows there through by way of the compressed gas inlet 110. As known to those skilled in the art, as shown in FIG. 2, as the gas jet exits the gas orifice 114, a region of low pressure is created such that liquid from the liquid reservoir 120 is drawn up through a liquid flow passage 230 that has an outlet 232 adjacent to the gas orifice 114. For instance, the opening diameter of the gas orifice 114 can range from 0.2 to 0.6 mm, e.g., 0.2, 0.25, 0.3, 0.35, 0.4, 0.45, 0.5, 0.55 or 0.6 mm, including ranges between any of the foregoing values. In various embodiments, the liquid from the liquid reservoir is mixed with the gas and the liquid/gas mixture is directed against a primary baffle 220 where the liquid is aerosolized and can then be inhaled into a patient's respiratory tract.

Figure 3:
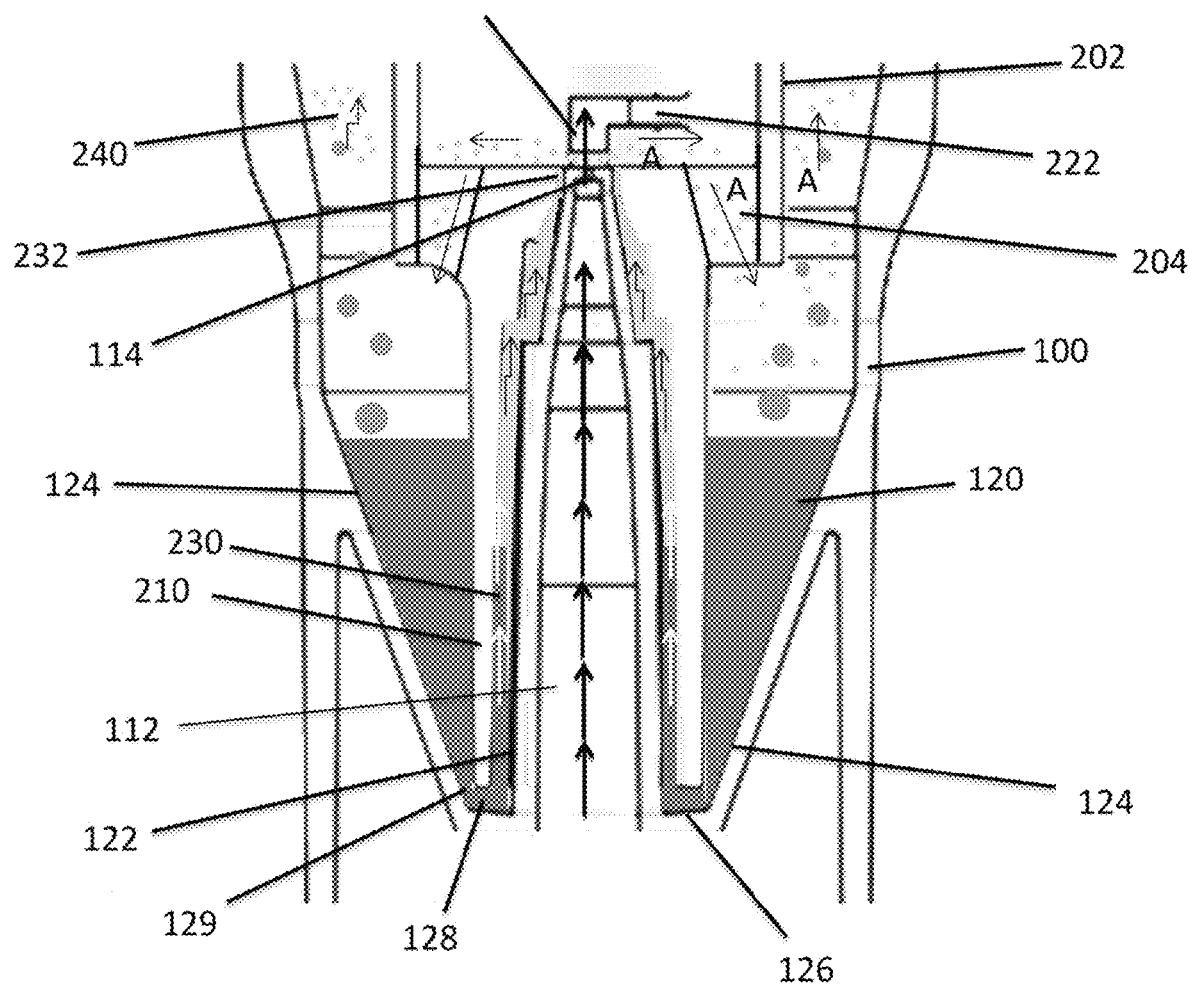
FIG. 3 is a detailed cross-sectional view of region I of FIG. 2 showing a liquid reservoir and a gas inlet nozzle disposed in the housing, a liquid flow channel disposed between the gas inlet nozzle and a sleeve portion of the flue, and a primary baffle proximate to a distal end of the nozzle.

Referring to FIG. 2, and particularly to region I thereof, a detailed view of which is shown in FIG. 3, liquid reservoir 120 is integrated within the main housing 100 and is located peripheral to (i.e., surrounding) the gas inlet nozzle 112 such that an inner sidewall 122 of the liquid reservoir 120 is formed by an outer surface of the gas inlet nozzle 112. In certain embodiments, the liquid reservoir 120 has a trapezoidally-shaped radial cross section, and includes a substantially planar bottom surface 126 adjacent to and surrounding the gas inlet nozzle 112. The planar bottom surface 126 may be arranged to be substantially orthogonal to an axial (e.g., vertical) dimension of the nebulizer. Liquid reservoir also includes a sloped, planar outer sidewall 124 disposed at an angle (θ) of, for example, 10 to 40° with respect to a central axis of the nebulizer, e.g., 10, 20, 30 or 40°, including ranges between any of the foregoing values, although lesser or greater angles can be used. The sloped liquid reservoir sidewall 124, which forms an inner wall of the main housing 100, is configured such that aerosol particles that settle on the sidewall 124 will cascade or drip back into the liquid reservoir 120.

Liquid reservoir 120 is configured to retain a specified volume of a liquid drug or medicament therein. For instance, the initial liquid volume can range from 0.5 to 2 ml, e.g., 0.5, 1, or 2 ml, including ranges between any of the foregoing values, although lesser or greater initial volumes can be used. Moreover, the liquid reservoir 120 is configured such that a relatively large fraction of the liquid volume initially contained in the reservoir can be nebulized. For instance, according to certain embodiments, 25 to 80% by mass of the liquid volume, e.g., 25, 30, 35, 40, 45, 50, 55, 60, 65, 70, 75 or 80%, including ranges between any of the foregoing values, can be nebulized during operation of the nebulizer. Example liquids include recombinant proteins such as interferon.

In embodiments, the tapered sidewall geometry of the liquid reservoir 120 funnels the liquid volume to a narrow vertical gap 128 at the base of the liquid reservoir between the bottom surface of the liquid reservoir and a downwardly-extending sleeve portion of the flue 200. In embodiments, the vertical gap 128 between an end portion of the sleeve 210 and the bottom surface 126 of the liquid reservoir 120 is less than 2 mm. For instance, vertical gap may measure 0.5 to 2 mm, e.g., 0.5, 0.75, 1, 1.25, 1,5, 1.75 or 2 mm, including ranges between any of the foregoing values. Furthermore, a tolerance gap 129 measured orthogonally from the sloped sidewall 124 to the flue sleeve 210 is less than 0.75 mm, e.g., 0.25, 0.3, 0.4, 0.5, 0.6, 0.7 or 0.75 mm, including ranges between any of the foregoing values. The cross-sectional shape of the liquid reservoir, including steep sidewalk, the relatively narrow vertical gap 128 between the bottom of the reservoir and the end surface of the flue sleeve 210, as well as the relatively narrow gap 129 between the sloped sidewall 124 and the flue sleeve 210 allow efficient uptake and utilization of the liquid volume within the liquid reservoir 120.

During use, the residual (e.g., un-nebulized) volume of liquid within the liquid reservoir can be less than 70% of the original charge, e.g., 30, 40, 50, 60 or 70%, including ranges between any of the foregoing values. Moreover, for a given volume of nebulized liquid, the disclosed jet nebulizer can generate an effective particle size distribution of particles. For instance, in contrast to many commercial systems, the disclosed jet nebulizer can generate a useful fraction, i.e., a respirable mass (RM), of aerosol particles that is greater than 50% of the aerosol output, i.e., an inhaled mass (IM). For instance, the respirable mass (RM) can be 55, 60, 70, 80, 90, 92, 94, 96, 98 or 99% of the inhaled mass, including ranges between any of the forgoing values.

Referring to FIGS. 1 and 2, the assembled nebulizer includes a flue 200 that is inserted within the body of the main housing 100. In certain embodiments, the main housing 100 and the flue 200 are respectively provided with cooperating tabs or notches 101, 201 in order to ensure a proper orientation of the flue within the main housing 100.

As seen in FIG. 3, flue 200 includes a sleeve 210 located at one end thereof that, when assembled, cooperates with the gas inlet nozzle 112 to define an annular liquid flow passage 230 therebetween. In embodiments, the outlet 232 of the liquid flow passage 230 has an annular shape defined by the top end of the flue sleeve 210 and the gas inlet nozzle 112. The gas outlet orifice 114 has a circular shape and is concentric with respect to the outlet 232 of the liquid flow passage 230.

The radial width (w) of the liquid flow passage, i.e., between the inlet nozzle 112 and the sleeve 210 may be constant or variable and, in certain embodiments, may be 0.1 to 0.5 mm, e.g., 0.1, 0.12, 0.15, 0.2, 0.25, 0.3, 0.4 or 0.5 mm, including ranges between any of the foregoing values. For instance, the radial width of the liquid flow passage may vary along an axial dimension of the nebulizer 10. The radial width of the liquid flow passage 230 is configured to efficiently transport liquid volume from the liquid reservoir 120 to outlet 232.

Upper portions of the flue 200, including upper portions of the sleeve 210, cooperate with inner walls of the main housing 100 to form an aerosol passage 240. That is, aerosol passage 240 may comprise a substantially annular passage that is located between an outer wall 202 of the flue 200 and inner surfaces of the housing 100. As noted above, during operation, pressurized gas flow passes through the gas inlet nozzle 112, exits gas orifice 114, and impinges upon a primary baffle 220 creating a localized vacuum that draws liquid up from the liquid reservoir 120 through the liquid flow passage 230 via the Venturi effect. The sonic jet passing through the gas orifice 114 and the entrained liquid strike the lower surface of the primary baffle 220 causing nebulization of the liquid.

Primary baffle 220 is axially aligned with and spaced apart from gas orifice 114. The primary baffle 220 is attached to an inner surface of the flue 200 above the gas inlet nozzle 112 via radial-extending ribs 222. The primary baffle 220 in the illustrated embodiment comprises a substantially circular disk having a planar lower surface, though in other embodiments the primary baffle 220 may present a non-planar and/or a non-circular lower surface, such as a rectangular, square-shaped or cupped (e.g., concave or convex) lower surface. A substantially circular primary baffle 220, for example, may have a diameter of 1 to 3 mm, e.g., 1, 1.5, 2, 2.5 or 3 mm, including ranges between any of the foregoing values. In certain embodiments, the diameter of the primary baffle 220 may be 1 to 10 times the opening diameter of the gas orifice 114. It will be appreciated that the dimensions of the gas orifice 114, primary baffle 220, as well as the proximity of the gas orifice 114 to the primary baffle 220 can be selected to control the pressure-flow relationship of the nebulizer.

By way of example, the distance from the exit of gas orifice 114 to the primary baffle 220 can range from 0.2 to 1 mm, e.g., 0.2, 0.3, 0.4, 0.5, 0.6, 0.7, 0.8, 0.9 or 1 mm, including ranges between any of the foregoing values, which has been found to be suitable to allow complete mixing of the sonic jet and the entrained liquid without substantially reducing the velocity of the resulting spray. For example, in one embodiment, the distance from the exit of gas orifice 114 to the primary baffle 220 can range from 0.5 to 1 mm.

The produced aerosol is drawn via an annular gap 204 between the flue sleeve 210 and an inner surface of the outer wall 202 of the flue 200 through aerosol passage 240 and around first and second secondary baffles 260, 270 to the aerosol outlet 130 Where it may be inhaled. The motion of the aerosol particles is shown by arrows (A) in FIGS. 3-5. As shown in FIG. 2, the second secondary baffle 270 is axially displaced from the first secondary baffle 260. The secondary baffles prevent a free sweep of the aerosol particles through the nebulizer to the patient. In embodiments, the secondary baffles operate to impede the passage of larger aerosol particles through the aerosol passage 240 and divert such large particles to the liquid reservoir 120 at the bottom of the main housing 100. For example, larger aerosol particles (e.g., greater than 10 microns) can fall onto the sloped sidewall 124 of the liquid reservoir 120 from where they can be recycled into the liquid reservoir.

Figure 4:
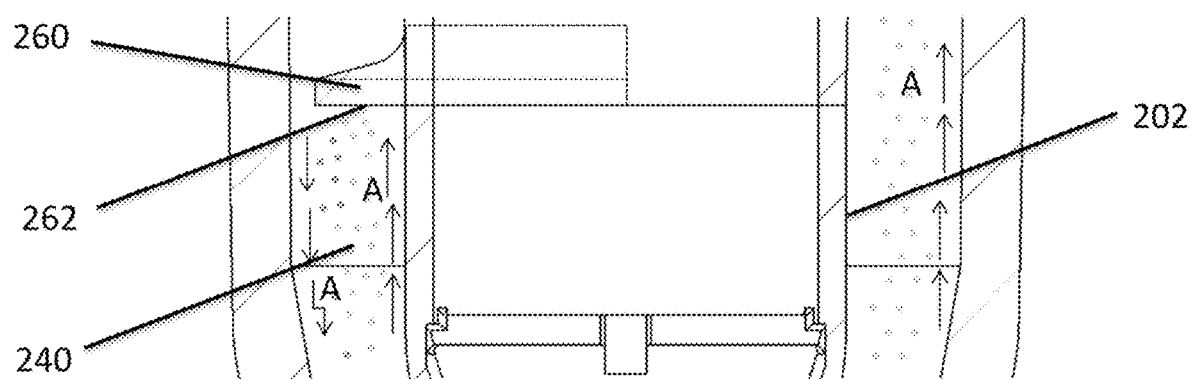
FIG. 4 is a detailed cross-sectional view of region II of FIG. 2 showing a first secondary baffle extending from an outer surface of the flue into an aerosol passage located between the flue and the housing.
Figure 5:
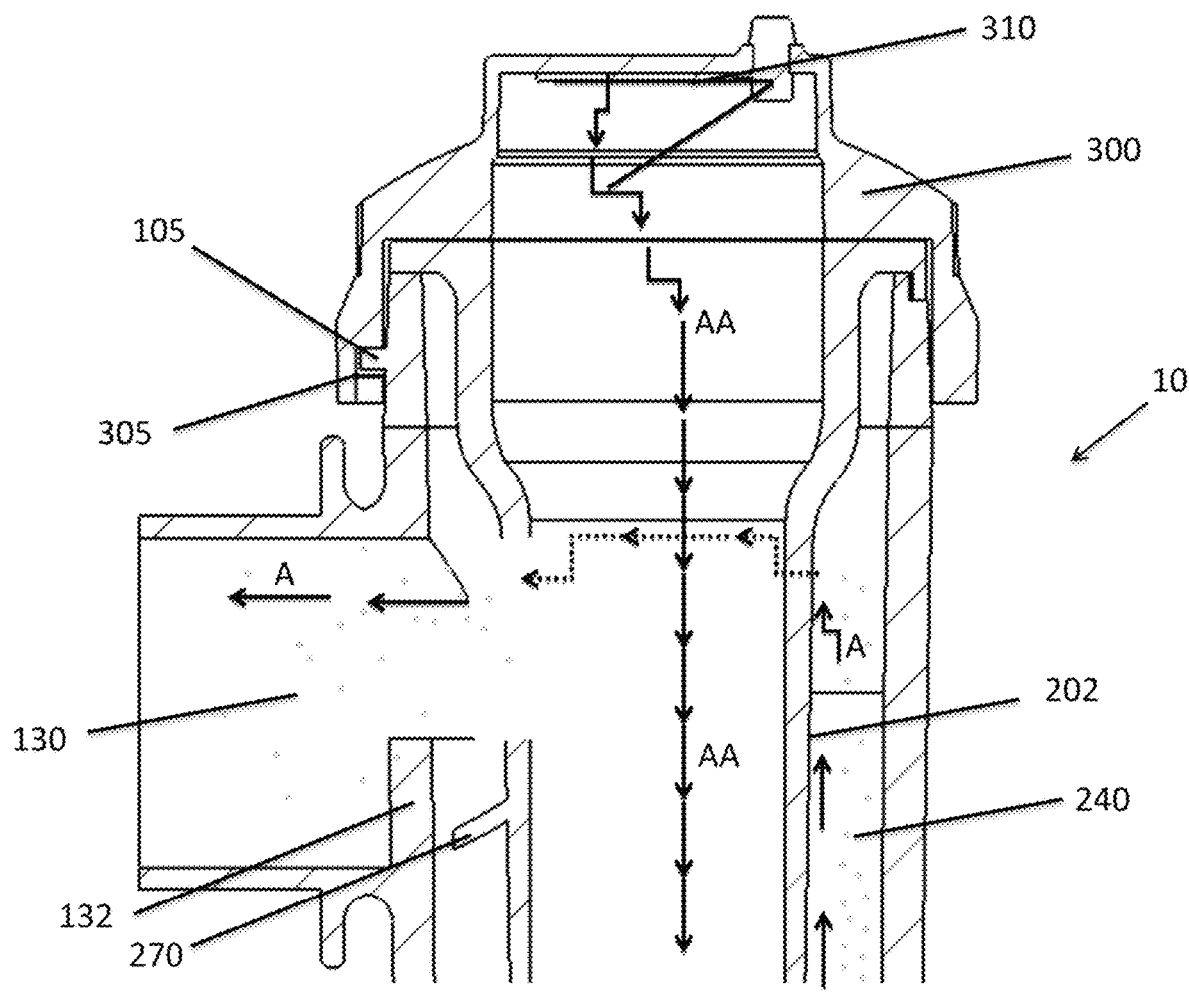
FIG. 5 is a detailed cross-sectional view of region III of FIG. 2 showing a second secondary baffle extending from an outer surface of the flue into the aerosol passage proximate to the aerosol outlet of the housing.

Referring to regions II and III of FIG. 1, which are shown in detail in FIGS. 4 and 5, respectively, first and second secondary baffles 260, 270 extend radially from a portion of an outer surface of the flue 200 into aerosol passage 240 and define a gap with an inner wall of the housing. The size of the gap between first and second secondary baffles 260, 270 and the inner wall of the housing may independently range from 0.2 to 0.8 mm, e.g., 0.2, 0.25, 0.3, 0.35, 0.4, 0.45, 0.5, 0.55, 0.6, 0.65, 0.7, 0.75 or 0.8 mm, including ranges between any of the foregoing values, although larger and smaller values are contemplated. In another embodiment, the size of the gap between first and second secondary baffles 260, 270 and the inner wall of the housing may independently range from 0.2 to 0.5 mm In various embodiments, the secondary baffles 260, 270 are disposed over less than the full circumference of the flue 200, and extend through an arc in a plane perpendicular to a central axis of the nebulizer of, for example, 45° to 180°. Thus, first and second secondary baffles extend partially around an outer surface of the flue 200 above sleeve 210, and are configured to project into aerosol passage 240 when the flue is inserted into the housing, i.e., during use of the nebulizer and disrupt the flow of aerosol particles to aerosol outlet 130.

As illustrated in FIG. 4, first secondary baffle 260 extends radially from a portion of an external surface of the flue 200 and comprises substantially planar ledge 262 forming a bottom surface thereof. The radial width of the ledge 262 may range from 0.5 to 1.2 mm, e.g., 0.5, 0.6, 0.7, 0.8, 0.9, 1, 1.1 or 1.2 mm, including ranges between any of the foregoing values. As shown schematically, upward-moving aerosol particles within aerosol passage 240 can collide with first secondary baffle 260, i.e., at ledge 262. The first secondary baffle 260 can affect the flow path of the aerosol particles and, for example, redirect their motion downward.

As with the first secondary baffle 260, second secondary baffle 270 is disposed within aerosol passage 240 upstream of the aerosol outlet 130. In various embodiments, second secondary baffle 270 comprises an arcuate cross section having a sloped bottom surface. The second secondary baffle 270 can affect the flow path of the aerosol particles and, for example, redirect their motion downward.

First and second secondary baffles 260, 270 are positioned to block larger aerosol particles traveling within aerosol passage 240 and inhibit their flow to the aerosol outlet 120. According to various embodiments, first and second secondary baffles 260, 270 are positioned proximate to the aerosol outlet 130 and create an upstream tortuous path, e.g., between the gas orifice 114 and the aerosol outlet 130, and during operation of the nebulizer direct larger aerosol particles downward where they coalesce and drip back into liquid reservoir 120. Secondary baffles 260, 270 comprise a surface that causes large particles to fall out of suspension, thus reducing the overall average particle size of the aerosol.

Aerosol particles that reach the aerosol outlet enter mouthpiece 400 from where they may be inhaled. In embodiments, the mouthpiece 400 is attached to the aerosol outlet 130 and is configured to convey aerosol particles to a patient. For instance, mouthpiece 400 may be attached to the aerosol outlet 130 by a friction fit. In various embodiments, aerosol outlet 130 includes a weir 132 that partially obstructs the outlet in order to mediate the flow of gases and aerosol particles therethrough. Increasing the resistance at the inspiratory port can increase help a patient control inspiration to effect slow and deep breathing, which can maximize aerosol deposition in the deep lung.

Aerosol production, including average particle size and particle size distribution, as well as the total output, i.e., during inhalation, may be enhanced by the (one-way) exhalation valve 420 incorporated into the mouthpiece and the attendant negative pressure created by a patient's inspiratory effort. Such breath-enhanced aerosol production leads to greater drug delivery, a larger fine-particle fraction, and less drug loss during expiration. In various embodiments, aerosol is directed through aerosol passage 240 by the back pressure created by the patient's inhalation.

In addition to mouthpiece exhalation valve 420, top cap 300 includes a (one-way) inhalation valve 310 that allows ambient air to flow into the main housing 100 during inhalation while preventing aerosol from escaping during exhalation. In certain embodiments, inhalation valve 310 comprises a relatively small areal dimension, i.e., the area through which inhaled air flows, which increases the velocity of inhaled air within the nebulizer and also induces a patient to inhale more slowly, which beneficially encourages inhaled aerosol to penetrate deeper into the patient's lungs.

When a patient inhales through the opening 410 of the mouthpiece 400, the inhalation valve 310 in top cap 300 is opened. Ambient air flows through the inhalation valve 310 and into the main housing. The flow of ambient air is shown in FIG. 5 with arrows (AA). The ambient air co-mingles with aerosol particles within the main housing and flows, together with the aerosol particles, through aerosol passage 240, and exits the main housing via aerosol outlet 130. Both ambient air and the aerosol particles pass through mouthpiece 400 and opening 410 and are inhaled by the patient.

Figure 6:
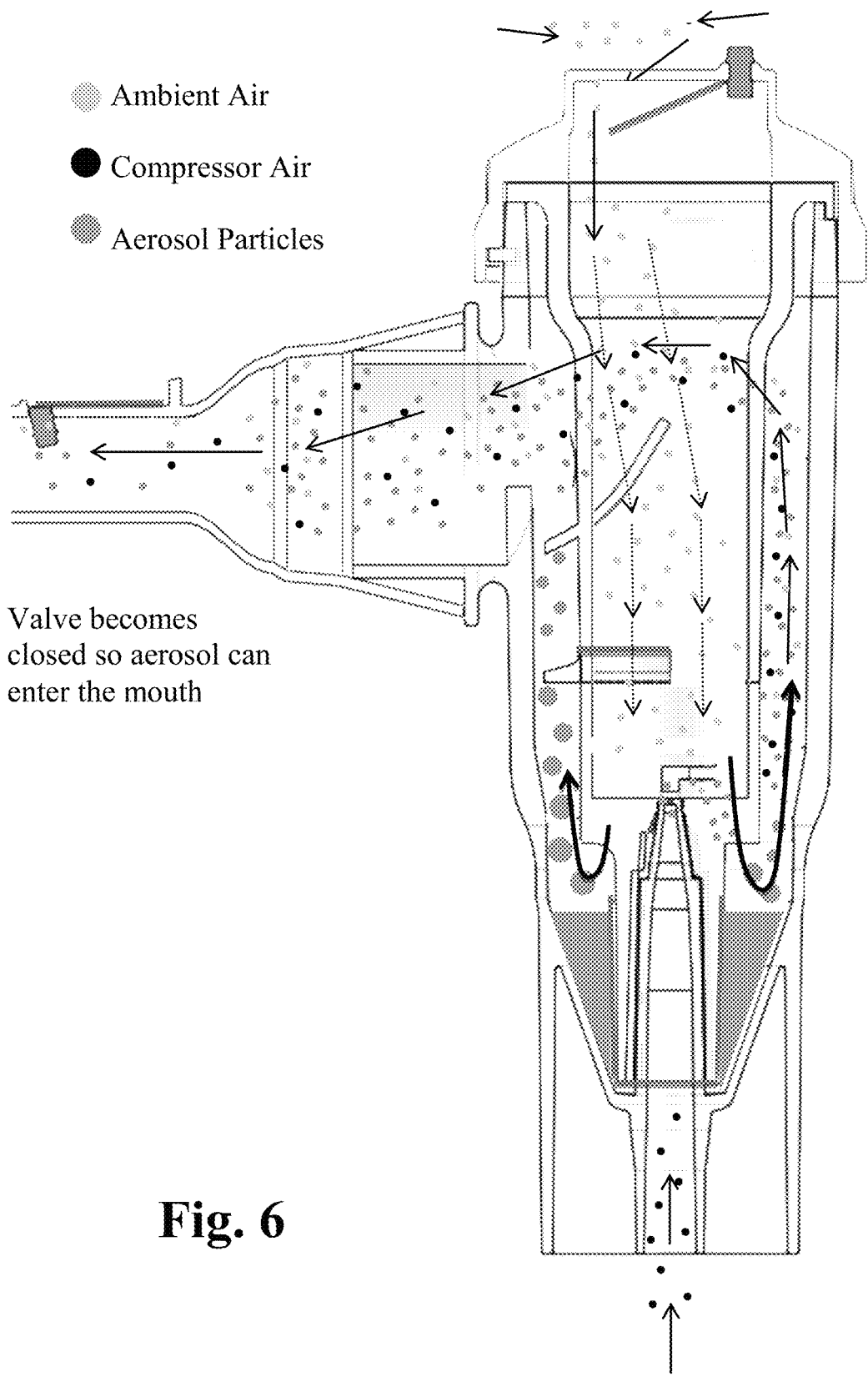
FIG. 6 is a flow diagram for an assembled jet nebulizer illustrating the motion of aerosol particles and gases when inhaling according to certain embodiments.
Figure 7:
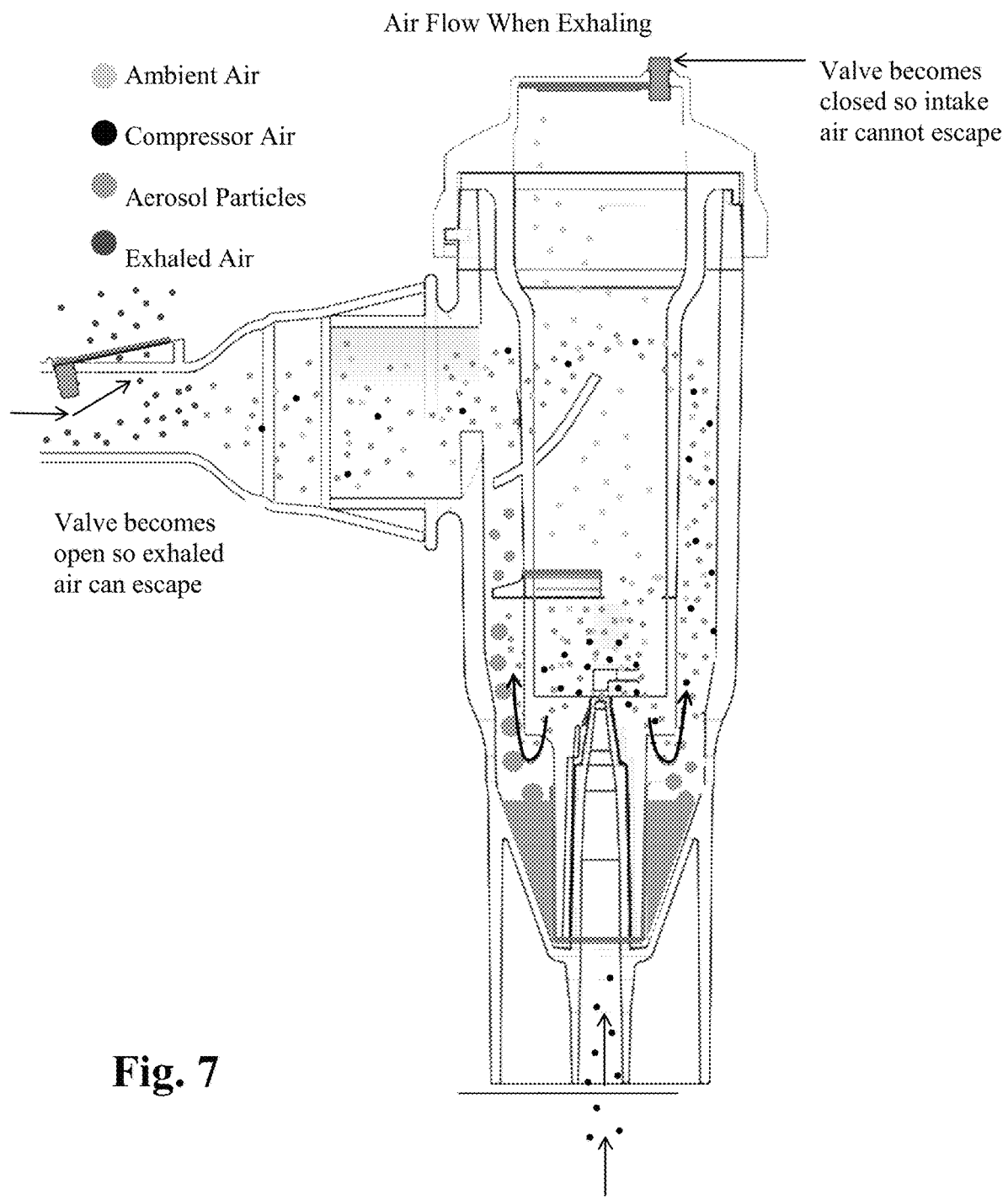
FIG. 7 is a flow diagram for an assembled jet nebulizer illustrating the motion of aerosol particles and gases when exhaling according to certain embodiments.

When a patient exhales into the opening 410 of the mouthpiece 400, the exhalation valve 420 is opened so that the respiratory air is discharged into the surroundings. The inhalation valve 310 is closed when the patient exhales, which prevents aerosol particles within the nebulizer from being vented into the surroundings. Gas and particle flow within an example nebulizer are shown in FIGS. 6 and 7 for inhaling and exhaling conditions, respectively.

As will be appreciated, the output particle size and particle size distribution can be controlled by the geometry of, inter alia, the gas orifice 140, primary baffle 220, liquid flow passage 230, and the configuration of the secondary baffles 260, 270.

EXAMPLES

The following examples are illustrative of various embodiments of the invention.

As used herein, an "aerosol" is a colloidal system of solid or liquid particles dispersed in a gas (e.g., air) and includes both the particles and the suspending gas.

Unless indicated to the contrary, when a range is provided, it is understood to be inclusive of the endpoints thereof as well the values therebetween. Thus, for example, the range of 0.5 to 1.0, includes the endpoints 0.5 and 1.0, but also the values therebetween.

The term "aerodynamic diameter" ($d_{ae}$) is used to express the aerodynamic behavior of an irregularly-shaped particle in terms of the diameter of an idealized particle. The aerodynamic diameter is the diameter of a sphere of unit density that has aerodynamic behavior identical to that of the particle in question. Thus, particles having the same aerodynamic diameter may have different shapes and dimensions. The "mass mean aerodynamic diameter" (MMAD) is calculated as the geometric mean of the aerodynamic diameters of a given sample of particles, e.g., inhaled particles.

The "inhalable aerosol fraction" is the fraction of total airborne particles that enter the body through the nose and/or mouth during breathing. This fraction corresponding to particles having a particular aerodynamic diameter (e.g., $d_{ae} \leq 100$ µm) is relevant to health effects throughout the respiratory tract, such as rhinitis, nasal and lung cancer as well as systemic effects. The term "respirable aerosol fraction" (or alveolar fraction) is the sub-fraction of the inhaled particles (e.g., $d_{ae} < 2.5$ µm) that penetrate into the alveolar region of the lungs (i.e., the respiratory bronchioles, and alveolar ducts and sacs). The respirable mass (RM) of a given aerosol volume can be expressed as the product of the inhalable mass (IM) and the respiratory fraction (RF), i.e., RM=RF*IM. The term "tidal volume" is the lung volume representing the volume of air displaced between normal inhalation and exhalation when extra effort is not applied.

In exemplary methods, compressed gas at high pressure (e.g., 5 to 50 psi, such as 5, 10, 25 or 50 psi, including ranges between any of the foregoing values) enters the nebulizer 10 at the compressed gas inlet 110 and travels into the gas inlet nozzle 112. Example gases include oxygen and air. At the upper end of the gas inlet nozzle 112, the gas passes through gas orifice 114 and is converted to a sonic jet of high speed gas. As liquid is entrained into the gas jet flow, additional fluid is drawn up through the liquid flow passage 230 from the liquid reservoir 120. Jet flow with entrained liquid impinges the bottom surface of primary baffle 220 and forms an aerosol.

In various embodiments, resultant aerosol particles, typically in the size range of greater than 0 to 10 µm pass through the aerosol passage 240 and exit the nebulizer via mouthpiece 400, while aerosol particles larger than 10 µm generally fail to escape the aerosol passage 240 and are recycled.

In vitro testing was performed using a DeVilbiss traveler compressor (3.1 liters/min flow, 11 psi). The nebulizer was filled with radiolabeled saline, and tested during simulated breathing using a piston ventilator. Ventilation conditions included a breathing cycle consistent with chronic obstructive pulmonary disease (COPD), and idealized slow-and-deep breathing. Expiratory gas exited via an expiratory valve in the mouthpiece or a valved holding chamber, such as a modified valved holding chamber (InspiRx Inspira-Chamber (IC)).

The mass median aerodynamic diameter (MMAD), associated with quantifying the central tendency of aerodynamic particle size distributions (APSDs) of nebulizer-generated aerosols, is calculated based on a model that assumes an underlying log-normal distribution of the mass-weighted data.

Particle size distributions were measured with a cascade impactor. A mass balance was performed, measuring inhaled mass (IM), respiratory fraction (RF=all particles$\leq 2.5$ microns), and respirable mass (RM=RF*IM), as well as chamber-deposited particles and residual (un-nebulized) liquid volume.

Figure 8:
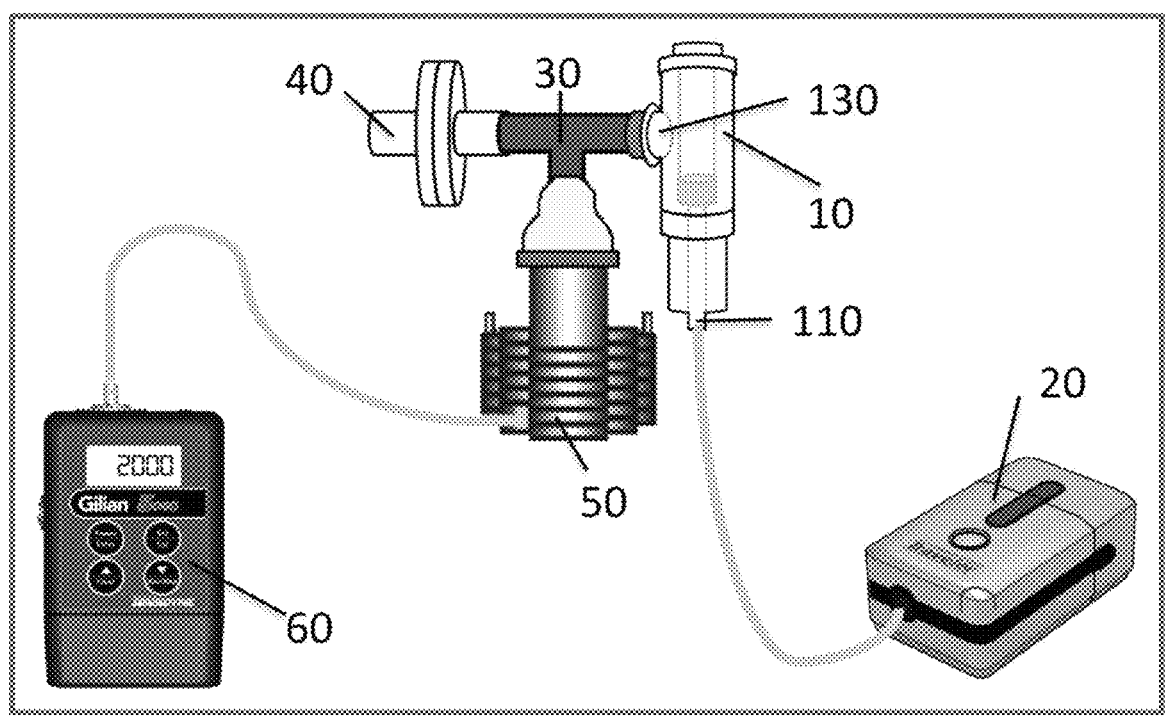
FIG. 8 is schematic diagram showing an experimental setup used to produce an unventilated, standing aerosol.

FIG. 8 is schematic diagram showing the experimental setup used to produce an unventilated, standing aerosol. Such a setup can be used, for example, to evaluate the aerosol output of a nebulizer, i.e., the amount of drug or medicament output that the nebulizer is capable of generating. Because the unventilated, standing aerosol is largely unmixed with ambient air, the aerosol is substantially saturated with water vapor.

Referring to FIG. 8, a gas compressor 20 is connected to the compressed gas inlet 110 of nebulizer 10, while the aerosol outlet 130 of the nebulizer 10 is connected to a T-connector 30. One output branch of the T-connector 30 is connected to an inhaled mass filter 40, while the second output branch of the T-connector 30 is connected to a cascade impactor 50. A vacuum pump 60 is also connected to the cascade impactor 50, which serves to draw aerosol particles passing through the T-connector 30 into the cascade impactor at a desired flow rate. In certain tests, the flow rate provided by the vacuum pump 60 is less than the flow rate provided by the gas compressor 20. For instance, the flow rate induced by the vacuum pump 60 into the cascade impactor 50 can be about 2 liters/min, while the output of the gas compressor 20 can be about 3 liters/min.

The sum of the aerosol particles collected from the inhaled mass filter 40 and the cascade impactor 50 represents the aerosol output of the nebulizer. The cascade impactor 50 measures the particle size distribution of the aerosol output from a representative fraction of the total output.

Figure 9:
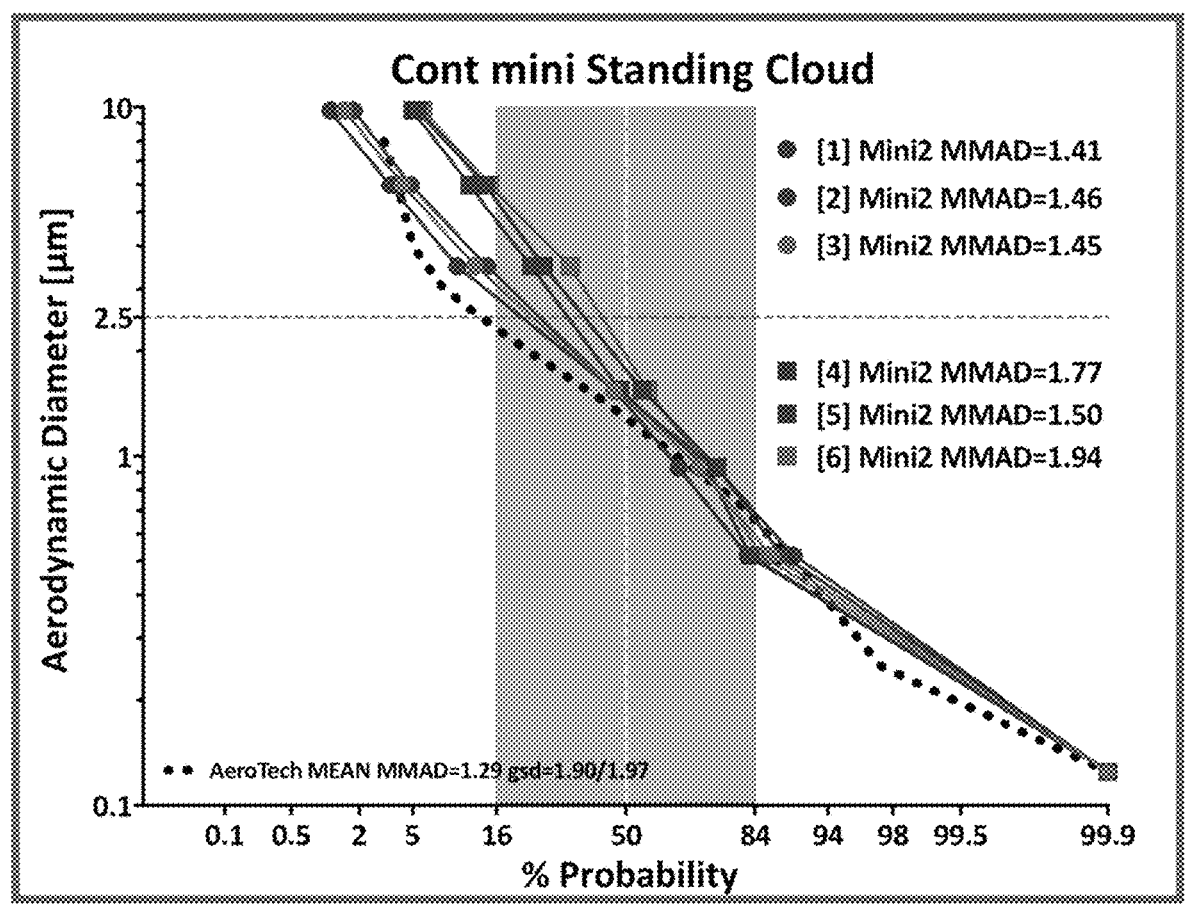
FIG. 9 is a plot showing the distribution of aerosol aerodynamic diameter for an unventilated, standing aerosol.

FIG. 9 is a log plot showing the distribution of aerosol aerodynamic diameter across six experimental runs for the unventilated, standing aerosol conditions (3.1 liters/min flow, 11 psi) associated with the apparatus of FIG. 8. Also plotted in FIG. 9 is average particle size distribution data from a commercially-available system that produces an aerosol distribution that does not result in a signification amount of upper airway deposition. It will be appreciated that particle size distribution data for nebulizers in accordance with various embodiments will fall below the benchmark data of the commercially-available system in a plot of the aerosol aerodynamic diameter versus percent probability, which is consistent with an aerosol population comprising a larger fraction of smaller particles.

From FIG. 9 (as well as FIGS. 13 and 16) the respiratory fraction (RF) can be calculated from the intercept of the plotted data with the line corresponding to an aerodynamic diameter of 2.5 microns. In each of FIGS. 9, 13 and 16, the shaded region from 16% to 84% represents one standard deviation of the log-normal distributed variable. According to various embodiments, the aerosol output of the nebulizer has a respiratory fraction of at least 70%, e.g., 70, 75, 80, 85, 90 or 95%, including ranges between any of the foregoing values.

Figure 10:
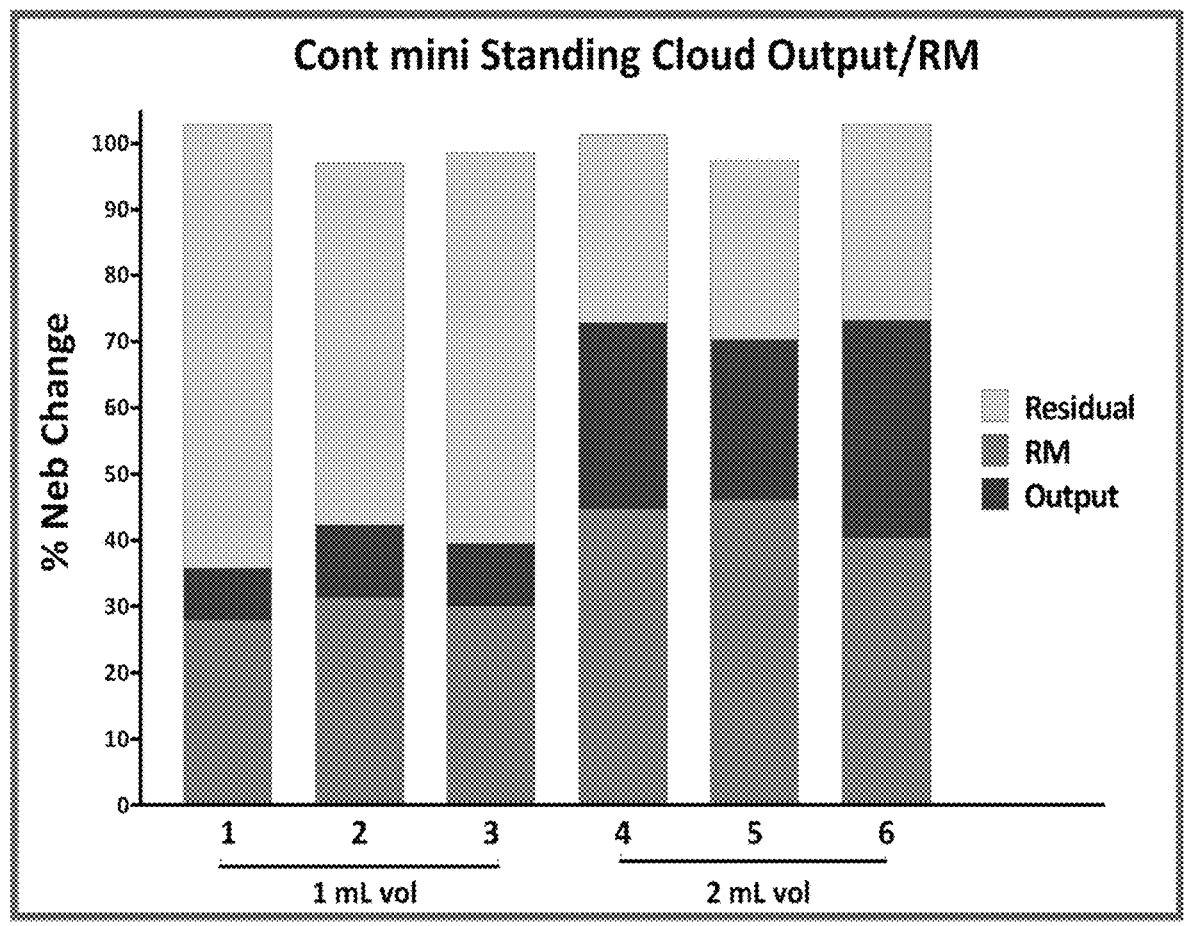
FIG. 10 is a plot showing the apportionment of recovered liquid volume for an unventilated, standing aerosol.

FIG. 10 is a graph showing the mass balance for the unventilated, standing aerosol formed using the apparatus of FIG. 8. As shown in FIG. 10, the inhaled mass (nebulizer output), which is plotted as a cumulative bar, is about 35-45% of the initial volume for an initial volume of 1 ml, and the inhaled mass is about 70-75% of the initial volume for an initial volume of 2 ml. In turn, for an initial liquid volume of 1 ml, the portion of the inhaled mass corresponding to the respirable mass (RM) is about 25-30% of the initial volume, while for an initial liquid volume of 2 ml, the respirable mass is about 40-50% of the initial volume.

Data from FIGS. 9 and 10 are tabulated in FIG. 11, where "RH %" stands for relative humidity, "Time" represents the run time of the experiment, "Vol" is the initial liquid volume or charge within the liquid reservoir 120, "Output" is the measured total aerosol output, "RM" is the respirable mass, which corresponds to the mass of the aerosol output having a particle size of less than 2.5 microns, and "Residual" is the measured amount of liquid or aerosol remaining within the nebulizer.

FIGS. 12A and 12B are schematic diagrams of experimental setups used to produce ventilated aerosols using a filtered mouthpiece or a valved holding chamber, respectively, in conjunction with the presently-disclosed nebulizer 10 according to various embodiments. Compared to the unventilated, standing aerosols, the ventilated aerosols more closely represent what is breathed by a patient.

The experimental setups shown in FIGS. 12A and 12B are similar to the experimental setup of FIG. 8 except, on the one hand, a piston ventilator 70 is used to provide ventilation and simulate the respiratory function of a patient. Furthermore, as shown in FIG. 12A, a filtered mouthpiece 80 is in fluid communication with the nebulizer downstream of the aerosol outlet 130 and upstream of the T-connector 30, while in FIG. 12B a chamber 90 is in fluid communication with the nebulizer downstream of the aerosol outlet 130 and upstream of the T-connector 30. In various embodiments, the chamber 90 may comprise a valved chamber and may be connected directly to the aerosol outlet, i.e., upstream of a mouthpiece 400.

The filtered mouthpiece 80 and the chamber 90 each comprise a one-way valve that functions as a surrogate for the one-way exhalation valve 420 found in a typical mouthpiece 400. For the purpose of measuring the quantity and distribution of aerosol particles produced by the nebulizer 10, the filtered mouthpiece 80 and the chamber 90 each further comprise a filter in fluid communication with the one-way valve that captures aerosol particles that would otherwise be vented to the surroundings during exhaling. An example chamber 90 has an internal chamber volume of 100 to 300 ml.

In various embodiments, the chamber 90 may include a baffle (not shown) that, together with the specified chamber volume, facilitates capture and conditioning of nebulized aerosol by mixing with room air, removing large particles by impaction, and providing better control of IM, RF, RM, and lung deposition.

During an inhale cycle, ambient air flows into and through nebulizer 10 via inhalation valve 310 in the top cap 300 of the nebulizer where it mixes with aerosol particles generated by the nebulizer. A portion of the aerosol particles that exit the nebulizer 10 are captured by the cascade impactor 50, while a majority of the aerosol particles that exit the nebulizer 10 are trapped by inhaled mass filter 40. Substantially aerosol-free gases enter piston ventilator 70.

During an exhale cycle, exhaled gas is vented to the surroundings via the one-way valve incorporated into filtered mouthpiece 80 or chamber 90. Thus, in the various experimental setups, filtered mouthpiece 80 and chamber 90 provide a pathway for gases to exit the system while trapping aerosol particles during exhalation.

In accordance with various embodiments, two ventilation conditions were studied. A first ventilation condition simulates the breathing cycle of a patient inflicted with chronic obstructive pulmonary disease (COPD). COPD is a progressive condition that makes it difficult to breathe, and may be caused, for example, by long-term exposure to lung irritants such as cigarette smoke, air pollution or chemical fumes. COPD disrupts the airflow in and out of the lungs and decreases lung function. COPD may include chronic bronchitis and/or emphysema. A second ventilation condition simulates slow and deep breathing of a subject.

The first ventilation condition (COPD condition) comprises a tidal volume ($V_T$) of 450 ml, a breathing frequency (f) of 15 breaths/min, and an inspiratory duty cycle (DC) of 0.35, where the inspiratory duty cycle is the ratio of inspiration time ($t_{in}$) to the total breath cycle time ($t_{tot}=t_{in}+t_{out}$). The second ventilation condition (slow and deep breathing) comprises a tidal volume of 1500 ml and a breathing frequency of 5 breaths/min.

Figure 13:
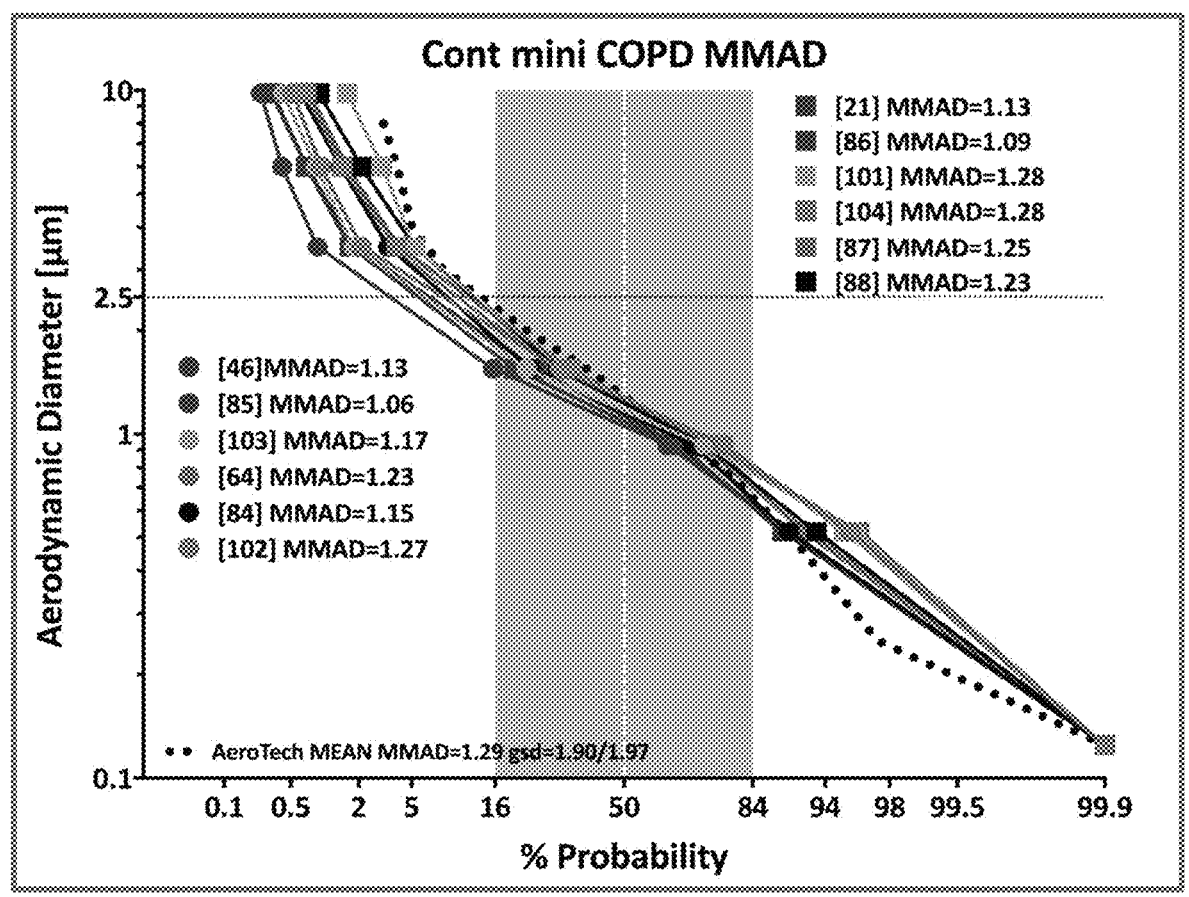
FIG. 13 is a plot showing the distribution of aerosol aerodynamic diameter for ventilated aerosols produced using the apparatus of FIGS. 12A and 12B, using a breathing profile consistent with chronic obstructive pulmonary disease (COPD)

FIG. 13 is a log-log plot showing the distribution of aerosol aerodynamic diameter for COPD ventilated aerosols produced using the apparatus of FIGS. 12A and 12B, including nebulizer 10. The data show a particle size distribution significantly improved with respect to the benchmark.

Figure 14:
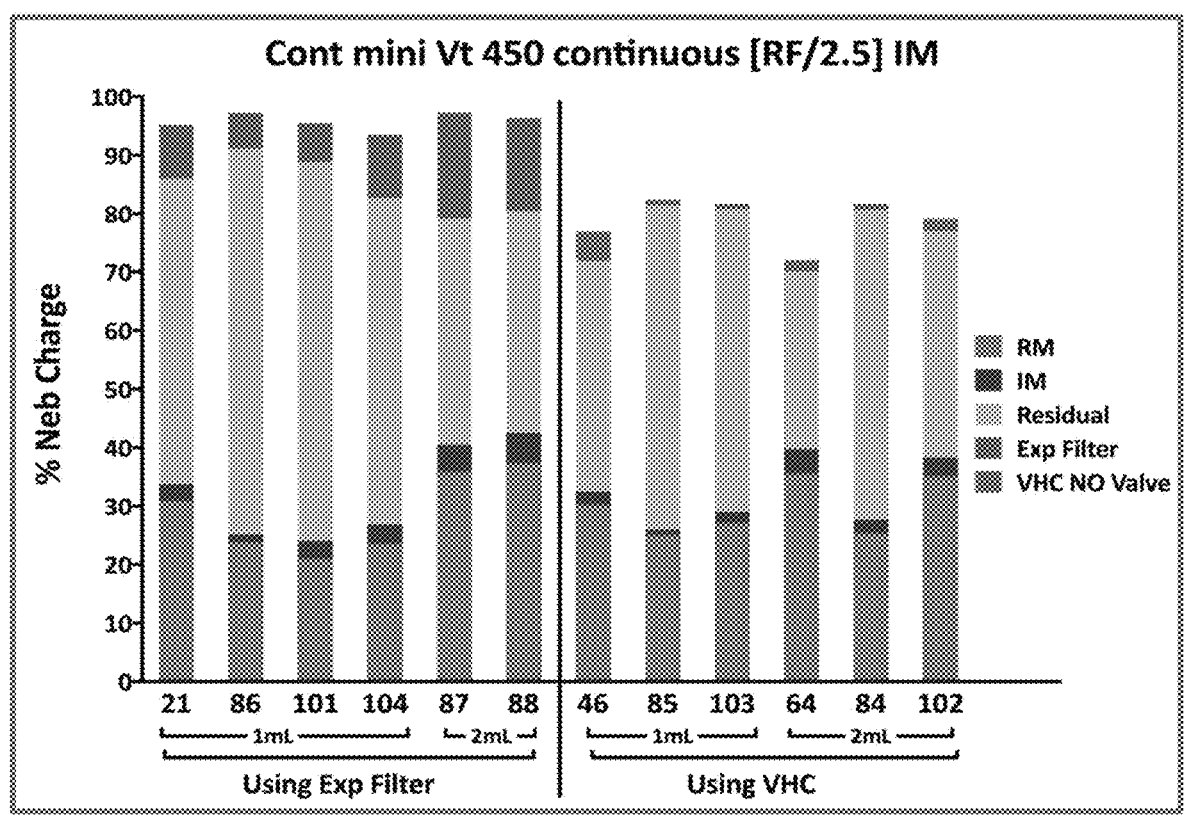
FIG. 14 is a plot showing the apportionment of recovered liquid volume for COPD ventilated aerosols produced using the apparatus of FIGS. 12A and 12B.

For the COPD breathing pattern, the liquid volume mass balance data is illustrated in FIG. 14, where the inhaled mass (IM) for the 1 ml and the 2 ml starting volumes is about 20-50% of the initial volume, and the respirable mass (RM) ranges from about 20-40% of the initial volume. Moreover, the respirable mass (RM) represents a substantial fraction of the inhaled mass (IM), such that the respiratory fraction (RF=RM/IM) ranges from about 85% to about 99%, e.g., 85, 90, 92, 94, 96, 98 or 99%, including ranges between any of the foregoing values.

Referring still to FIG. 14, and in connection with the filtered mouthpiece data, "Exp Filter" (or LEAK as reported in FIGS. 15 and 18) is the aerosol mass collected on the expiratory filter of the filtered mouthpiece 80, which corresponds to aerosol particles that would be exhaled by a patient. In connection with the chamber data, "VHC" is the portion of the aerosol particles collected in the valved holding chamber 90.

FIG. 15 is a table summarizing the aerodynamic diameter data and liquid volume recovery data from FIGS. 13 and 14.

Figure 16:
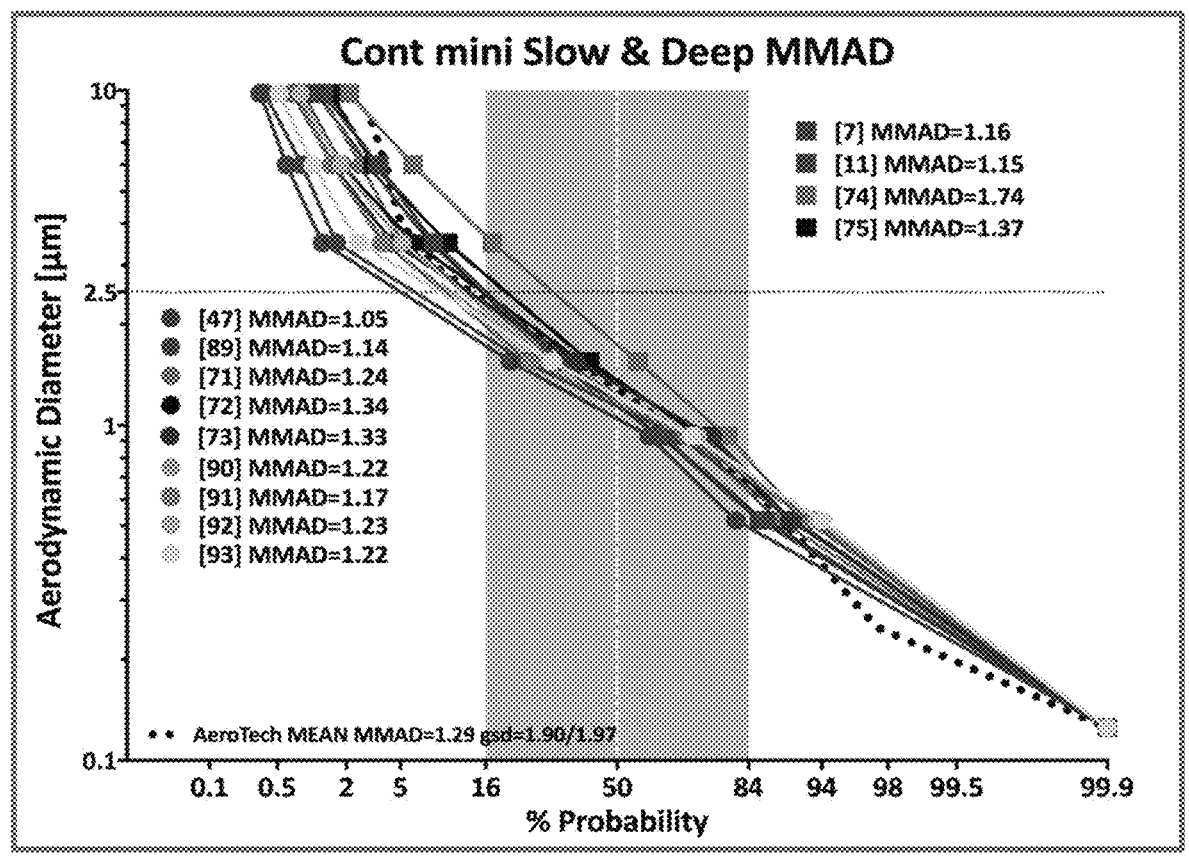
FIG. 16 is a plot showing the distribution of aerosol aerodynamic diameter for slow and deep ventilated aerosols produced using the apparatus of FIGS. 12A and 12B.
Figure 17:
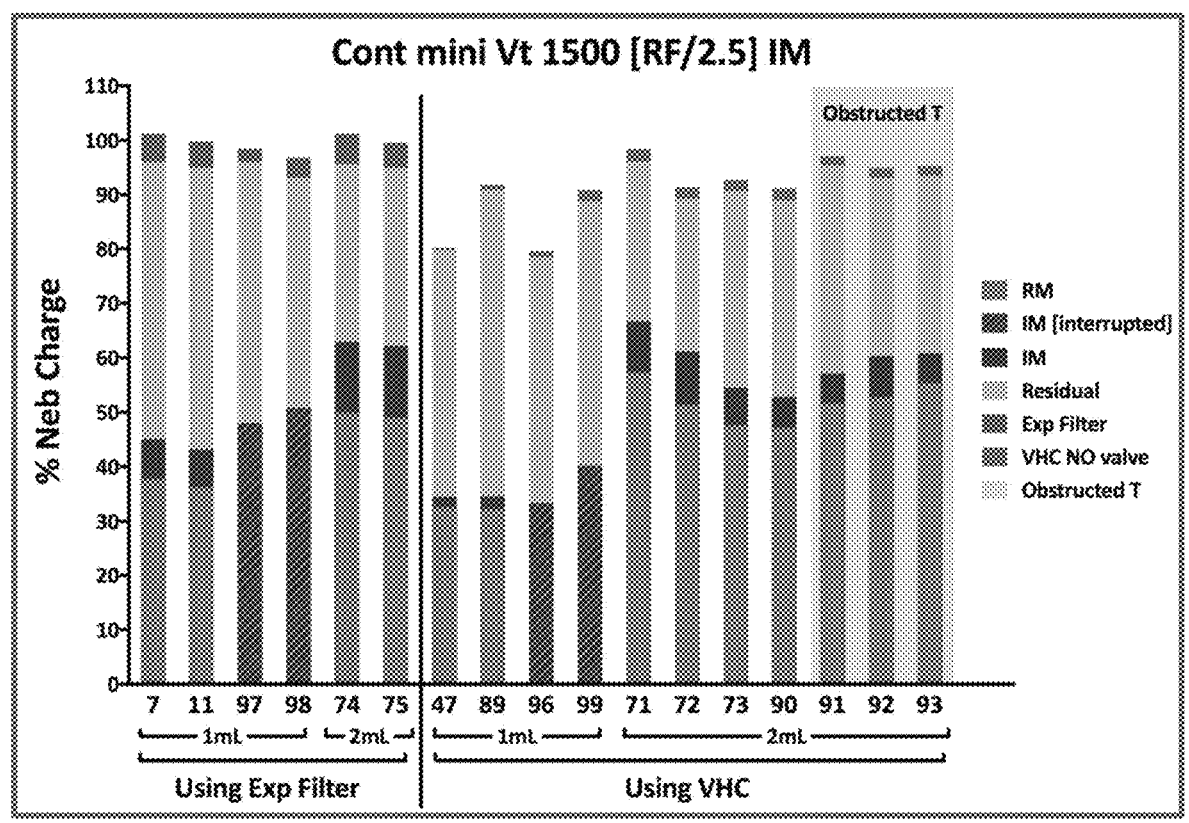
FIG. 17 is a plot showing the apportionment of recovered liquid volume for slow and deep ventilated aerosols produced using the apparatus of FIGS. 12A and 12B.

FIG. 16 is a plot showing the distribution of aerosol aerodynamic diameter for slow (e.g., 5 breaths/min) and deep (e.g., 1500 ml tidal volume) ventilated aerosols produced using the apparatus of FIGS. 12A and 12B, and FIG. 17 is a plot showing the apportionment of liquid volume for the slow and deep ventilated aerosols. Data in FIG. 17 to the left of the vertical partition represent use of the nebulizer with the filtered mouthpiece 80, while data to the right of the vertical partition correspond to a nebulizer comprising valved chamber 90.

Referring to FIG. 17 and the filtered mouthpiece data, the inhaled mass (IM) is about 40-50% of the initial volume for an initial volume of 1 ml, and about 60-65% of the initial volume for an initial volume of 2 ml. In turn, for an initial liquid volume of 1 ml, the respirable mass (RM) is about 35-40% of the initial volume, while for an initial liquid volume of 2 ml, the respirable mass is about 50% of the initial volume.

Referring still to FIG. 17 and the valved holding chamber (VHC) data, the inhaled mass (IM) is about 30-40% of the initial volume for an initial volume of 1 ml, and about 50-70% of the initial volume for an initial volume of 2 ml. In turn, for an initial liquid volume of 1 ml, the respirable mass (RM) is about 30-35% of the initial volume, while for an initial liquid volume of 2 ml, the respirable mass is about 45-60% of the initial volume. FIG. 18 is a table summarizing the aerodynamic diameter data and liquid volume recovery data from FIGS. 16 and 17. It will be appreciated that the respirable mass is a significant fraction of the inhaled mass for the slow and deep breathing cycle aerosols.

Breath enhancement and the attendant impact on aerosol production can be seen for the slow and deep breathing cycle aerosols with reference to run numbers 96-99 in FIGS. 17 and 18. In a breath enhanced nebulizer, the patient's inspiratory effect increases aerosol production and delivery of the drug or medicament. Moreover, without wishing to be bound by theory, it is believed that a majority of the aerosol production occurs during inhalation.

For instance, runs 7 and 11 were repeated as runs 97 and 98 but with the cascade impactor measurement omitted. Rather, for runs 97 and 98, the piston ventilator 70 was intentionally turned off for 30 seconds to simulate a patient disengaging from the nebulizer 10 while the nebulizer continued to operate.

Despite disengaging from the nebulizer, no significant loss of aerosol is observed, i.e., the amount of aerosol exiting the nebulizer while the patient is not breathing on it is relatively small. Thus, a patient disengaging from the nebulizer for 30 seconds would receive a substantially identical aerosol dose to a patient who maintained an uninterrupted breathing cycle.

Without wishing to be bound by theory, the relatively small loss of aerosol to the surroundings when the patient is not breathing on the mouthpiece may be attributed to the relatively low flow rate (e.g., 3 liters/min) of the gas compressor 20. In various embodiments, and in contrast to many commercially-available nebulizers, the compressed air flow rate into the nebulizer during use, i.e., can range from 1 to 10 liters/min, e.g., 1, 2, 3, 4, 5, 6, 7, 8, 9 or 10 liters/min, including ranges between any of the foregoing values.

The effect of the valved chamber 90 on the aerosol output can be seen, for example, with reference to runs 47 and 89. Compared to runs 7 and 11, although the total inhaled mass is slightly decreased, the quality of the aerosol is substantially improved. Specifically, the chamber-derived aerosols can be characterized by a respiratory fraction (RF) of greater than 90%, e.g., 92, 94 or 96%, including ranges between any of the foregoing values, compared to a respiratory fraction of about 84% for runs 7 and 11.

Minimizing the non-respirable portion ($d_{ae}>2.5$ microns) of the inhaled mass beneficially decreases upper airway deposition, which can otherwise cause unwanted side effects and additionally interfere with deep lung adsorption. According to embodiments, nebulizer 10 produces an aerosol that passes through a patient's upper airway without any significant upper airway deposition. In certain embodiments, the aerosol particle distribution is free of particles that will deposit in upper airways.

Figure 19:
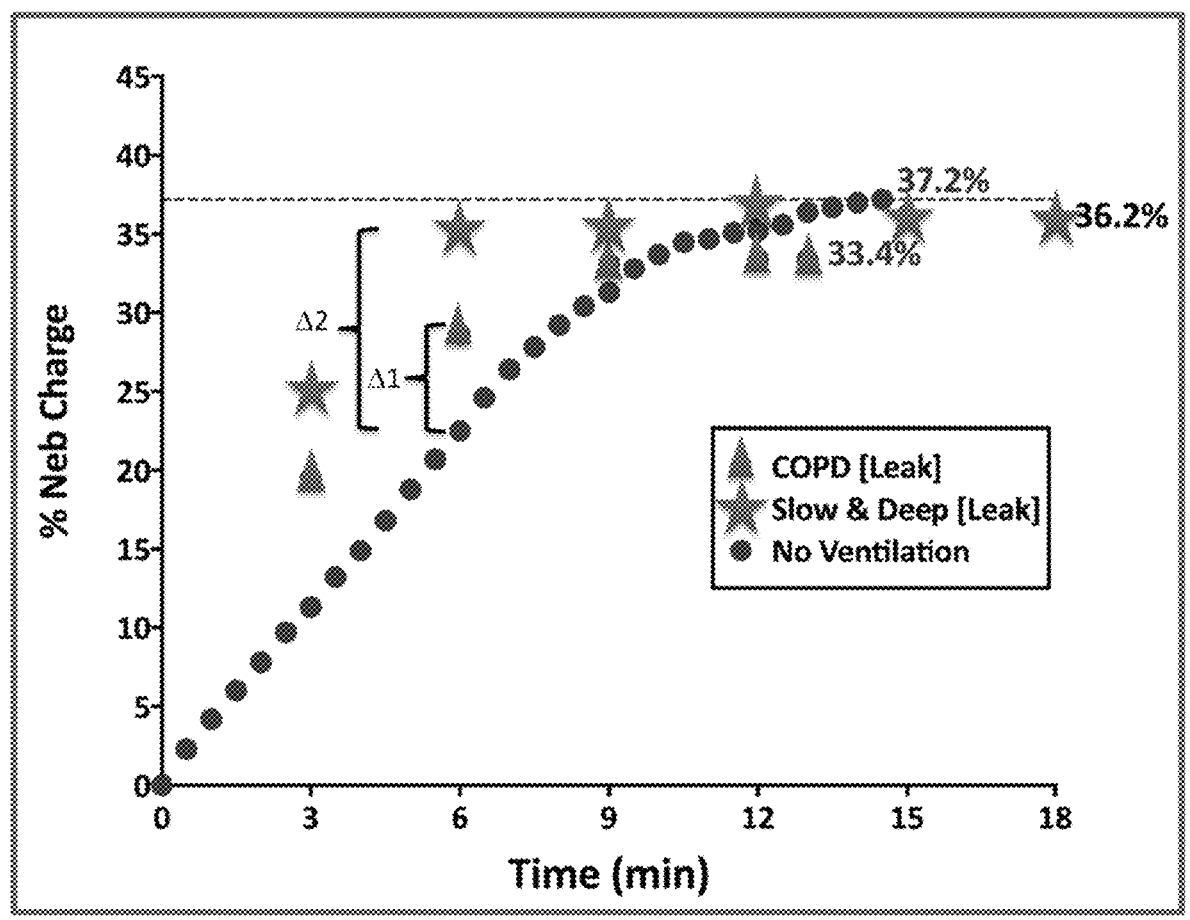
FIG. 19 is a plot of inhaled mass versus time for radiolabeled saline aerosols produced with an exemplary jet nebulizer using various breathing profiles.
Figure 20:
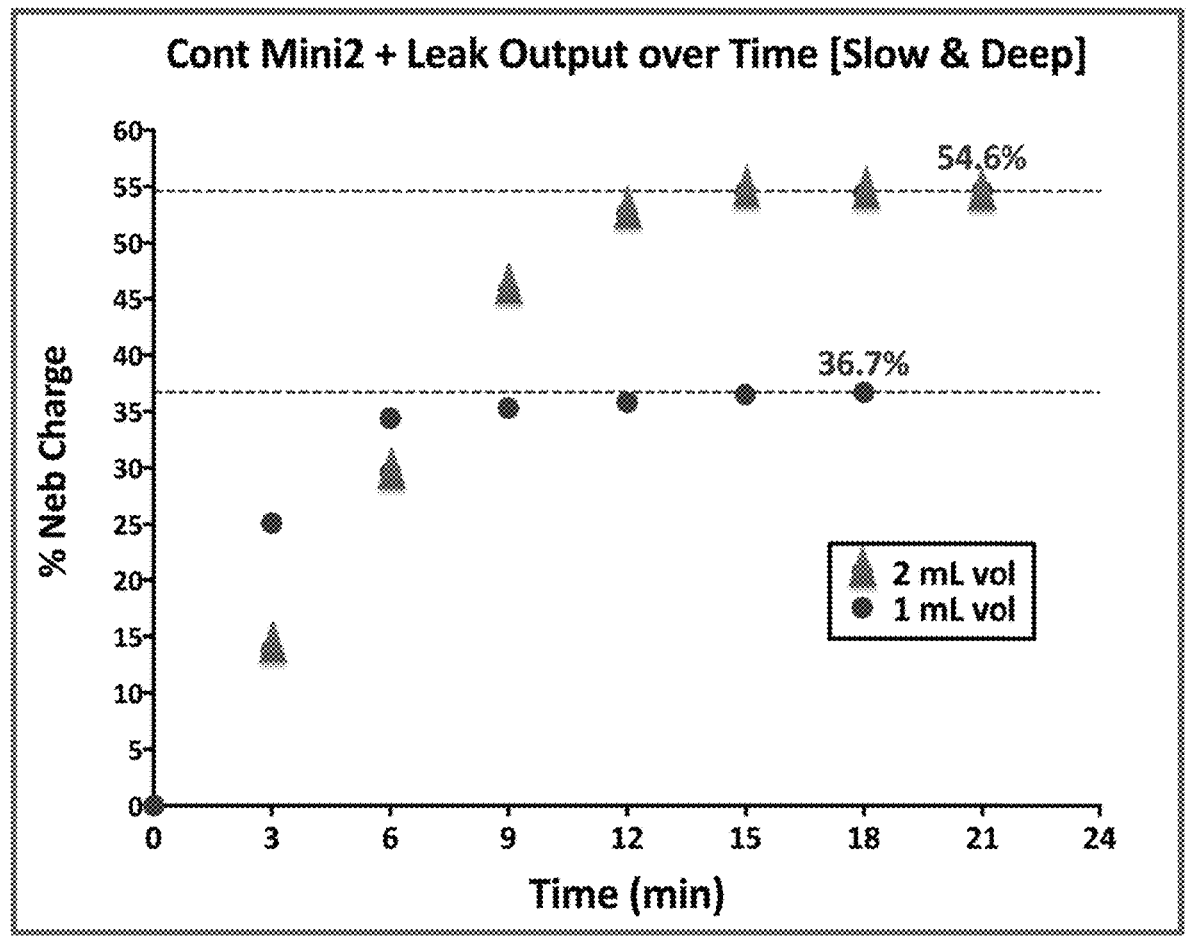
FIG. 20 is a plot of inhaled mass versus time for radiolabeled saline aerosols produced using different initial liquid volumes.

FIGS. 19 and 20 are plots of liquid consumption from the liquid reservoir versus time for different breathing conditions and different liquid starting volumes, respectively, where the amount of consumed liquid is the difference between the starting volume and the final volume of liquid within the liquid reservoir after aerosolization. In particular, the impact of the breath enhancement can be seen with reference to FIG. 19. For instance, under conditions of no ventilation, approximately 23% of the liquid volume has been nebulized after 6 min, compared with about 28% under COPD conditions and about 35% under conditions of slow and deep breathing. The respective differences in liquid utilization (Δ1 and Δ2) are highlighted.

The disclosed nebulizer is configured to operate with a small (e.g., less than 2 ml) initial volume of liquid drug or medicament, and can be used to treat both spontaneously-breathing patients and ventilated patients. Exemplary nebulizers can aerosolize greater than 50% of the starting liquid volume, e.g., 50, 60 or 70%, including ranges between any of the foregoing values, and produce an aerosol having a majority of particles less than 2.5 microns in diameter. In accordance with certain embodiments, the nebulizer 10 can be breath actuated or breath enhanced. An exemplary nebulizer 10 includes only a main housing 100, flue 200, top cap 300, and optional mouthpiece 400, which are readily assembled and disassembled.

Figure 21:
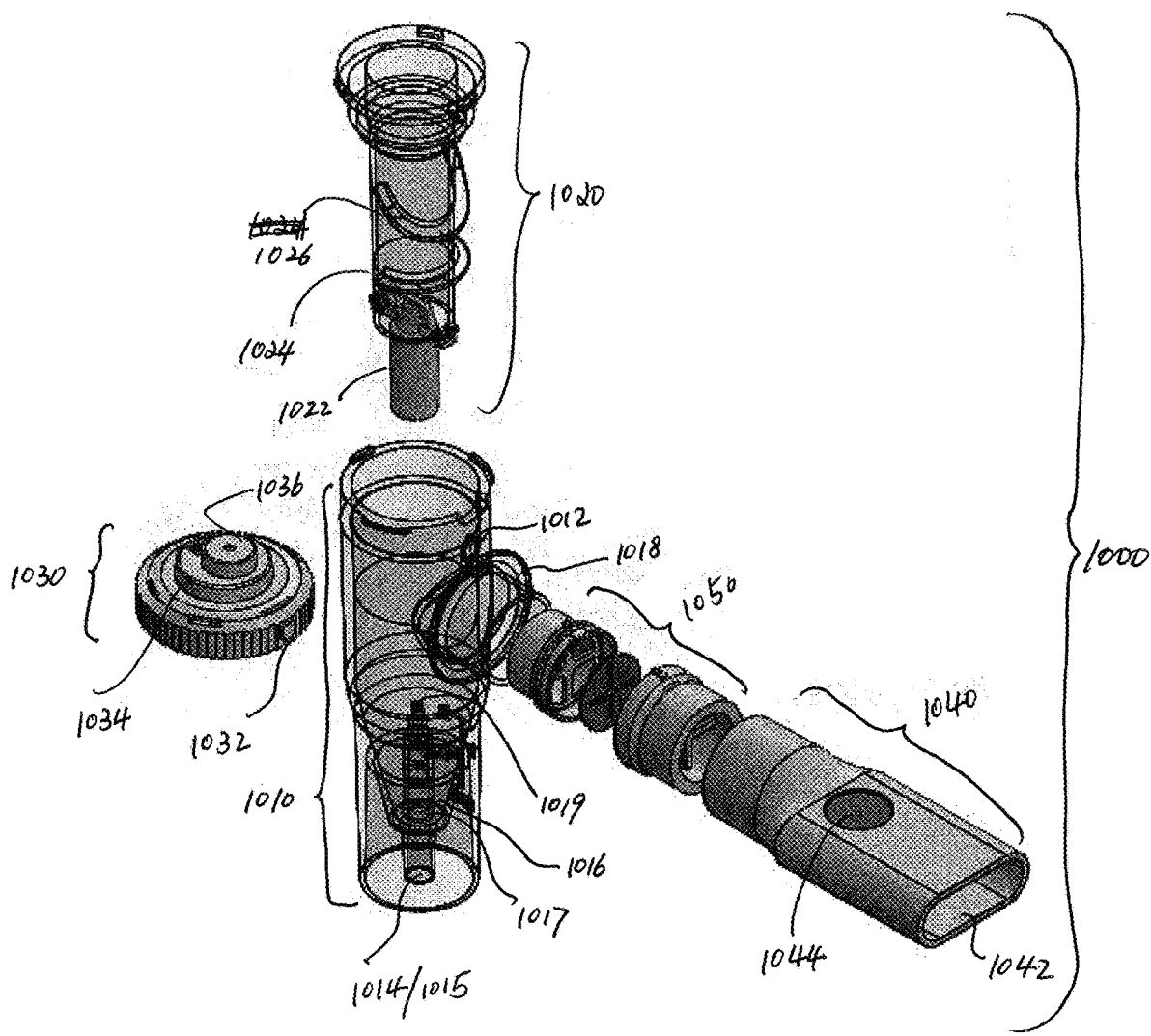
FIG. 21 is an exploded perspective view of a jet nebulizer according to another exemplary embodiment.

FIG. 21 illustrates another exemplary embodiment of a breath-enhanced jet nebulizer 1000. The nebulizer 1000 includes a main housing 1010 having a substantially cylindrical construction. The nebulizer 1000 further includes a substantially cylindrical flue 1020. The cylindrical flue 1020 includes a sleeve 1022 and a pair of baffles 1024 and 1026 that are configured to be inserted within the main housing 1010.

The nebulizer 1000 includes a top cap 1030, which is secured to the main housing 1010 for holding the flue 1020 within the main housing 1010 at a predetermined alignment. The top cap 1030 may be secured to the main housing 1010 by cooperative engagement of cap threads or cap notches 1032 with corresponding threads or tabs 1012 on the main housing.

The top cap 1030 includes an inhalation valve 1034, which is a one way valve. The inhalation valve 1034 allows ambient air to flow into the main housing 1010 during inhalation while preventing aerosol from escaping during exhalation. In certain embodiments, the inhalation valve 1034 has a relatively small areal dimension, i.e., the area through which inhaled air flows, which increases the velocity of inhaled air within the nebulizer and also induces a patient to inhale more slowly, which beneficially encourages inhaled aerosol to penetrate deeper into the patient's lungs. The inhalation valve 1034 has similar or same structural features as those of the inhalation valve 310 of the nebulizer 10 according to the previous embodiment.

According to the current embodiment, the top cap 1030 further includes an audible indicator 1036, which is in the form of a flow restrictor. The audible indicator 1036 functions to restrict inlet air flow, thereby allowing or facilitating slow and deep breathing, since slow and deep breathing is desirable for providing optimal particle size into the lung. The audible indicator (flow restrictor) 1036 offers unique benefits for small volume nebulizers.

The main housing 1010 includes a compressed gas inlet 1014, a liquid reservoir 1016 and an aerosol outlet 1018. The aerosol outlet 1018 is formed in a lateral sidewall of the main housing 1010. The compressed gas inlet 1014 includes a tubular gas passage 1015 that extends through a gas inlet nozzle 1017, which terminates at an upper distal end in a gas orifice 1019. In embodiments, gas and liquid are mixed together by passing a quickly-moving gas stream through the gas orifice.

The gas orifice 1019 is sized to provide a sonic gas jet as pressurized gas flows therethrough by way of the compressed gas inlet 1014. As explained previously, as a gas jet exits the gas orifice 1019, a region of low pressure is created, such that liquid from the liquid reservoir 1016 is drawn up through a liquid flow passage around the liquid reservoir. In various embodiments, the liquid from the liquid reservoir is mixed with the gas and the liquid/gas mixture is directed against a primary baffle (which is the same or similar as the primary baffle 220 of the nebulizer 10) where the liquid is aerosolized and can then be inhaled into a patient's respiratory tract.

The nebulizer 1000 further includes a mouthpiece 1040 that is attached to the nebulizer to deliver aerosol particles to a patient. The mouthpiece 1040 may be attached to the nebulizer by a friction fit. The mouthpiece 1040 includes an opening 1042 and an exhalation valve 1044. The exhalation valve 1044 is configured to open when a patient exhales into the mouthpiece 1040 via the opening 1042 and thereby exhaust the exhalation from the patient, and close when a patient inhales through the mouthpiece. Thus, the exhalation valve 1044 allows discharge of respiratory air during exhalation while inhibiting an inflow of ambient air during inhalation. The main housing 1010, the flue 1020, the top cap 1030 and the mouthpiece 1040 may be constructed of a polymer material and may be formed, for example, by casting, extrusion, or molding such as 3D blow molding.

For example, one or more of the components of the nebulizer 1000 can be formed from a polymer material such as thermoset and elastomeric monomers and polymers, and monomeric and polymeric thermoplastics including fluorocarbons, polyesters, polyamides, nylon, polybutadienes, polyvinyl chloride, silicone resins, polypropylene, as well as combinations and composites thereof.

The nebulizer 1000 further includes an inhalation orifice opening valve 1050 that is designed to manipulate the particle size that goes into the lung of a patient. The inhalation orifice opening valve 1050 can be fitted into the aerosol outlet 1018 at one end thereof and into the opening of the mouthpiece 1040 at the opposite end thereof. The inhalation orifice opening valve 1050 can define one or more central openings or one or more side openings during the inhalation of the user. As a result, the inhalation orifice opening valve 1050 improves the particle size to different extents, for allowing tailored particle sizes when they are required.

Figure 22:
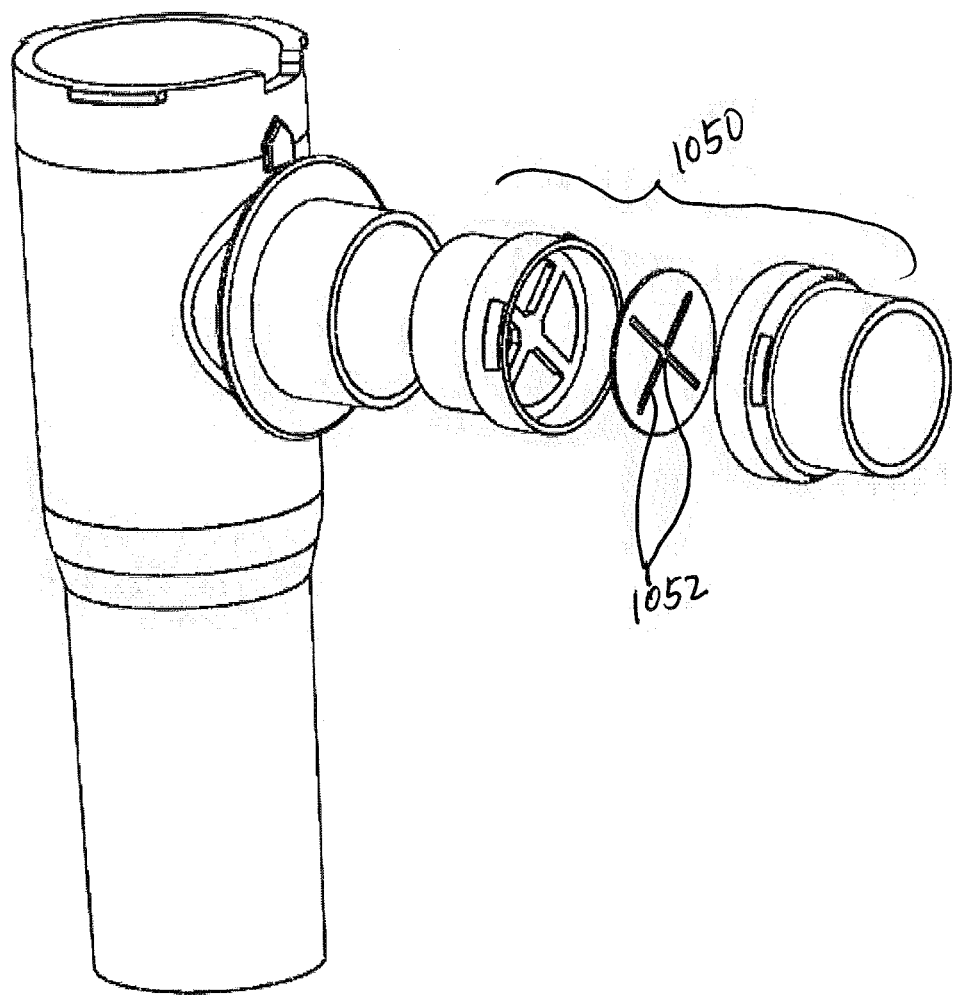
FIG. 22 is a perspective view of the jet nebulizer of FIG. 21, showing an embodiment of an inhalation orifice opening valve of the jet nebulizer.
Figure 23:
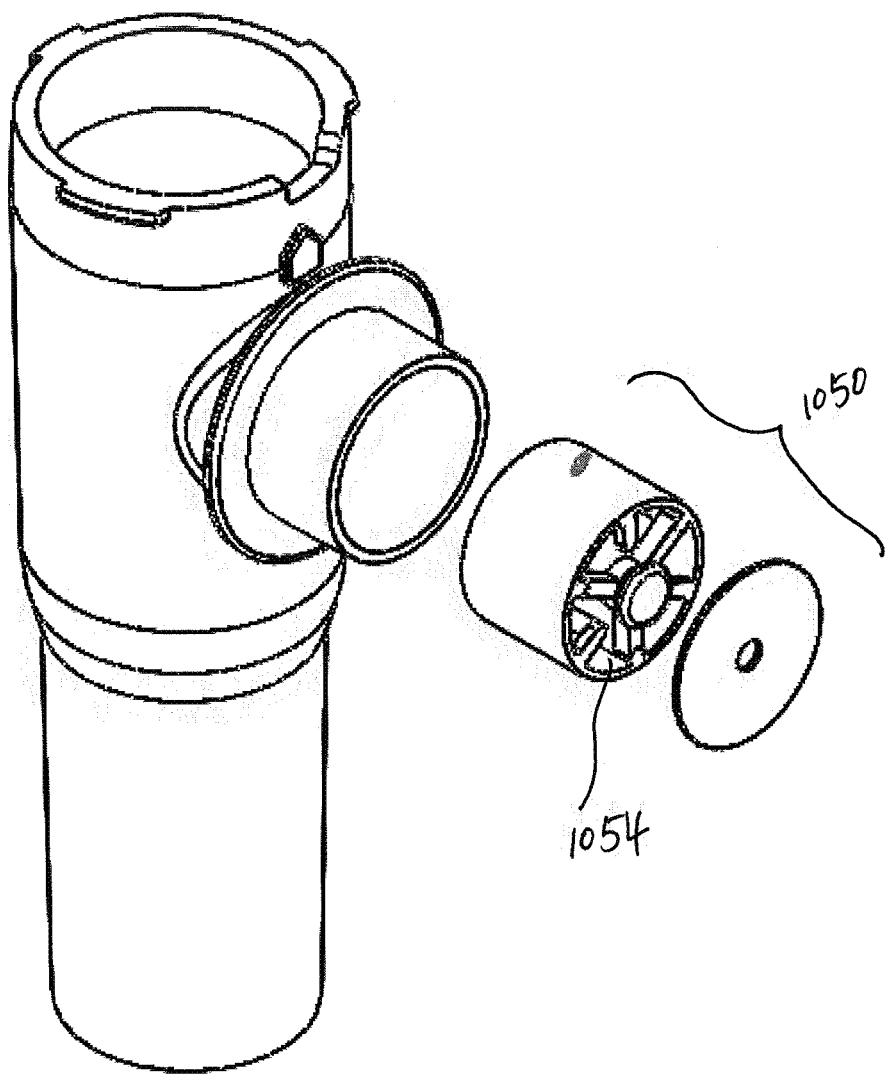
FIG. 23 is a perspective view of the jet nebulizer of FIG. 21, showing another embodiment of the inhalation orifice opening valve.

FIG. 22 illustrates a first embodiment of the inhalation orifice opening valve 1050, which provide one or more central openings 1052 when the user inhales through the nebulizer 1000. FIG. 23 illustrates a second embodiment of the inhalation orifice opening valve 1050, which provide one or more side opening 1054 when the user inhales through the nebulizer 1000.

Figure 24:
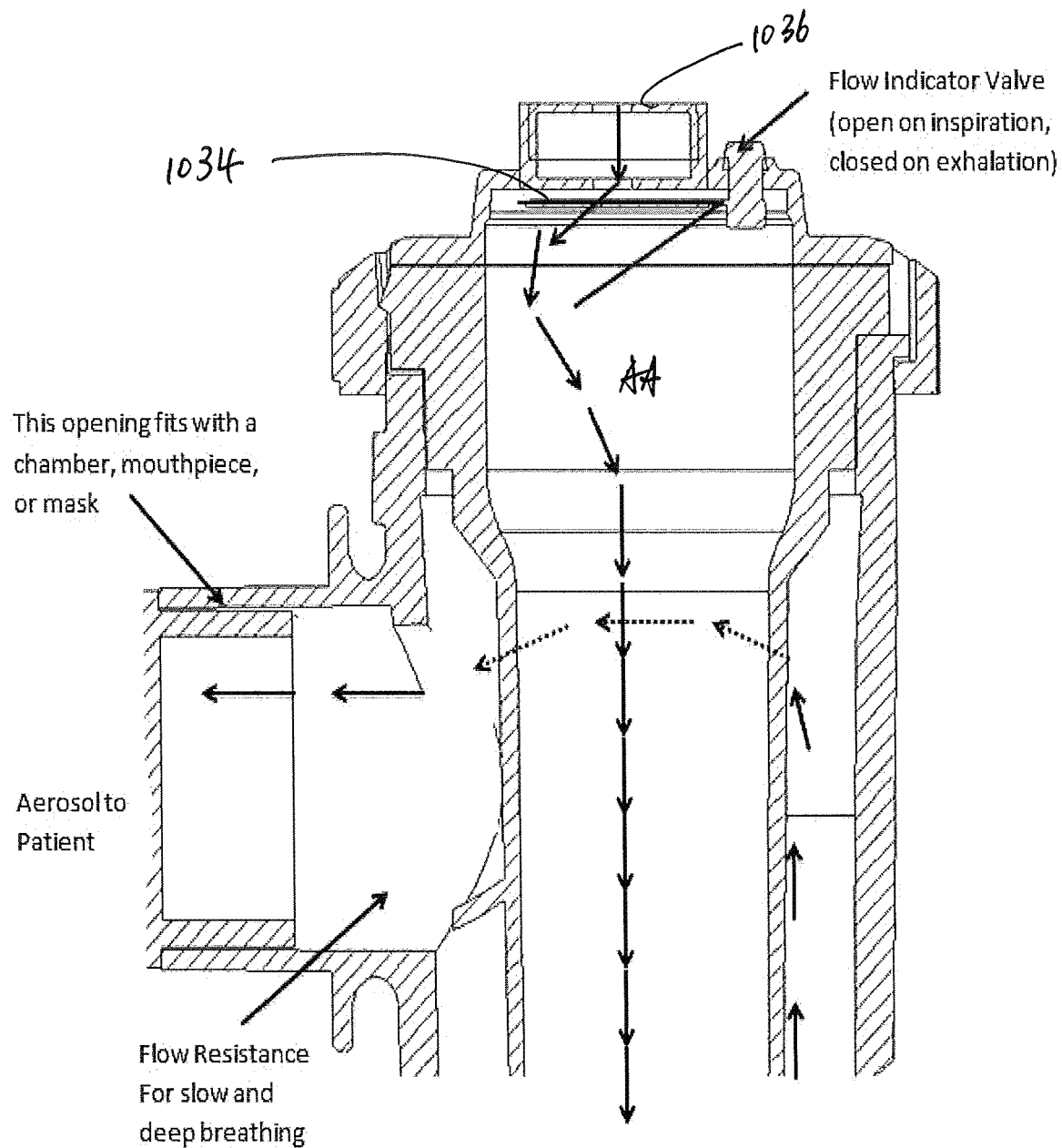
FIG. 24 is a partial cross section view of the jet nebulizer of FIG. 21, showing a flow of the ambient air and the aerosol.

When a patient inhales through the opening 1042 of the mouthpiece 1040, the inhalation valve 1034 in the top cap 1030 is opened. Ambient air flows through the audible indictor 1036 and the inhalation valve 1034 and into the main housing. The flow of ambient air is shown in FIG. 24 with arrows (AA). The ambient air co-mingles with aerosol particles within the main housing and flows, together with the aerosol particles, through the aerosol passage, and exits the main housing via the aerosol outlet. Both the ambient air and the aerosol particles pass through the mouthpiece and are inhaled by the patient. This process can be the same as the process shown in FIG. 5. According to the nebulizer 1000, the audible indicator 1036 can include an opening of about 2-4 mm, which restricts the flow of air that the patient breathes in. This allows for a slow and deep breathing by the patient. In addition, the opening of the audible indicator 1036 generates an audible signal that alerts the patient by whistling, when the patient is breathing overly fast. Thus, the audible indicator 1036 can be used as a training tool for the patient.

Figure 25:
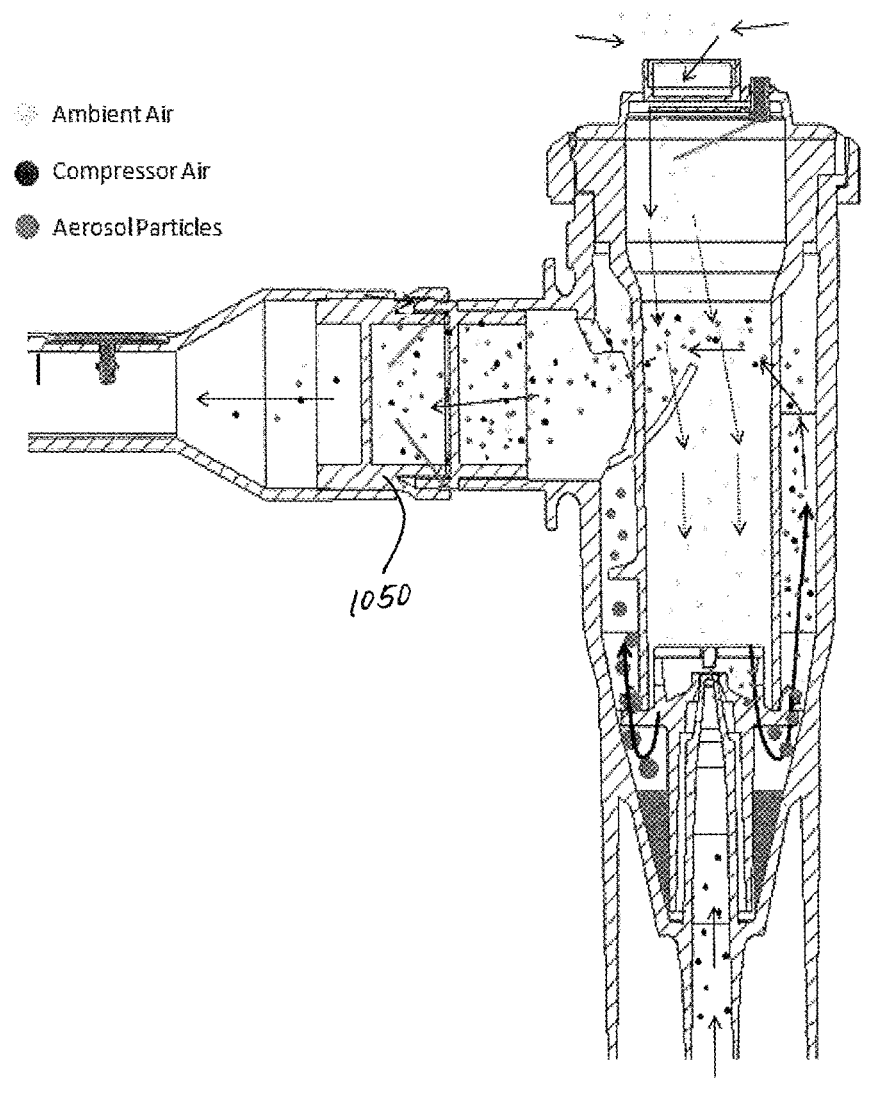
Figure 26:
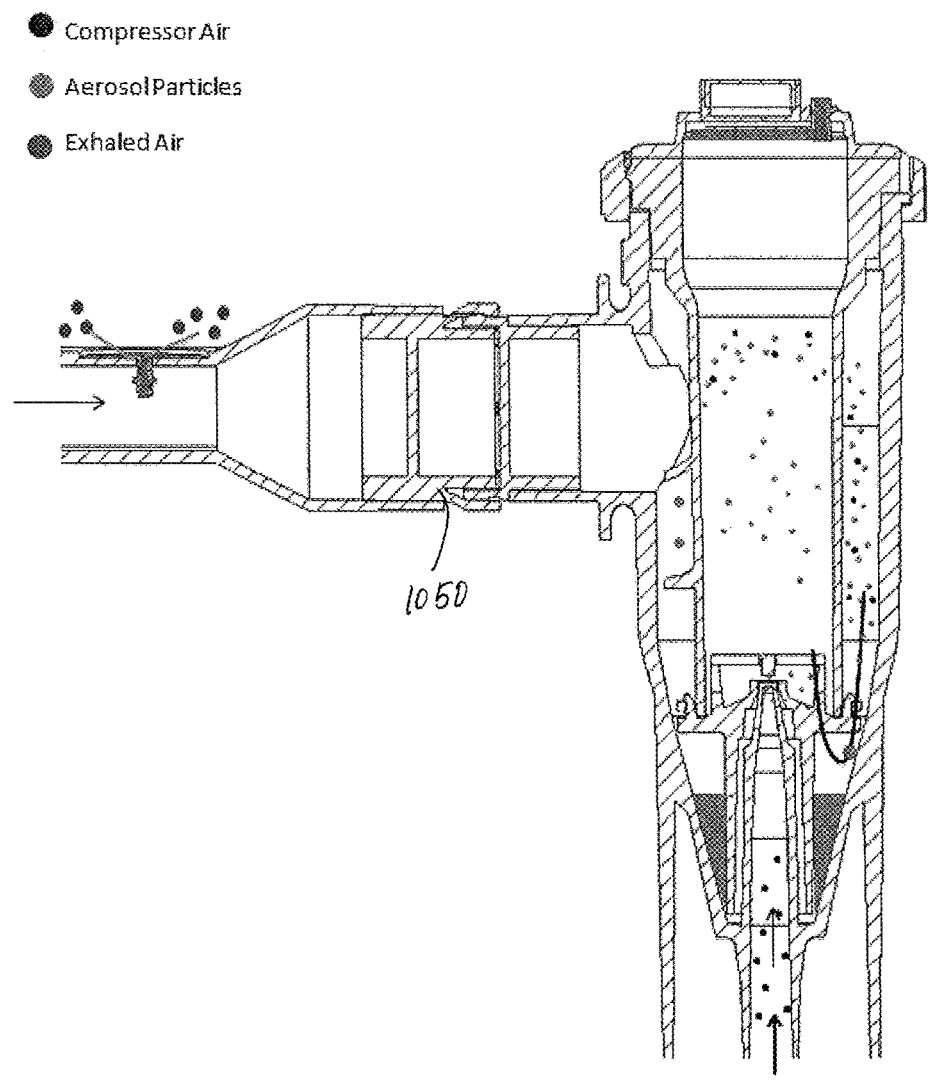

FIG. 25 shows the gas and particle flow within the nebulizer 1000 for inhaling condition. FIG. 26 shows the gas and particle flow within the nebulizer 1000 for exhaling condition. As shown in FIGS. 25 and 26, as the combination of the ambient air, the compressed air and the aerosol particles pass through the inhalation orifice opening valve 1050, the size of the aerosol particles can be adjusted or controlled by the central openings 1052 or the side openings 1054 of the inhalation orifice opening valve 1050, to thereby achieving tailored dimensions of the particles.

In another experiment, the apparatus of FIG. 12A was utilized using the InspiRx Mini nebulizer of FIG. 21 as the Mini Nebulizer with ("y") and without valves ("n"). In this experiment, a low flow compressor [3.8 LPM] generated saline aerosols radioactively labeled with $^{99m}Tc$. Using filters and a low flow cascade pump (impactor), aerosol, output and respirable mass ("RM") were measured for standing cloud ("SC") (no breathing), Ventilated ("V") slow and deep breathing ("S&D") (generated with a piston pump, tidal volume 1.5 Liters at a rate of 5 breathes per minute) ("BPM") and COPD breathing (tidal volume 0.45 liters, rate of 15 BPM. duty cycle 0.35). A mass balance was performed that included inhaled mass ("IM"), exhaled mass ("EM"), Respirable Fraction ("RF", all particles less than or equal to 2.5 μm), respirable mass ("RM") and nebulizer residual ("RES"). Various mass median aerodynamic diameters ("MMAD") were used. The results are indicated hereinbelow. In the table below, N stands for number of trials.

TABLE 1

| Condition | Valve | N | MMAD | IM* | RF* | RM* | RES* | EM* | Recovery* |
|---|---|---|---|---|---|---|---|---|---|
| SC | n | 3 | 1.8 ± 0.22 | 72 ± 1.6 | 0.62 ± 0.1 | 43.9 ± 3.0 | 28.5 ± 1.3 | — | 101 ± 2.8 |
| SC | y | 3 | 2.1 ± 0.44 | 51.6 ± 10.3 | 0.54 ± 0.1 | 27.6 ± 5.3 | 43.1 ± 11.4 | — | 100 ± 4.1 |
| V, S&D | n | 2 | 1.5 ± 0.04 | 60.8 ± 2.3 | 0.69 ± 0.0 | 41.9 ± 2.3 | 29.0 ± 2.9 | 12.7 ± 3.3 | 102 ± 2.5 |
| V, S&D | y | 3 | 1.3 ± 0.09 | 44.8 ± 4.6 | 0.87 ± 0.0 | 39.0 ± 2.3 | 36.1 ± 5.2 | 14.3 ± 1.5 | 105 ± 3.0 |
| V, COPD | y | 2 | 1.3 ± 0.09 | 21.8 ± 5.5 | 0.89 ± 0.0 | 19.3 ± 4.2 | 34.9 ± 2.5 | 37.7 ± 0.2 | 106 ± 3.6 |

*Data expressed as % Nebulizer Charge

Figure 27:
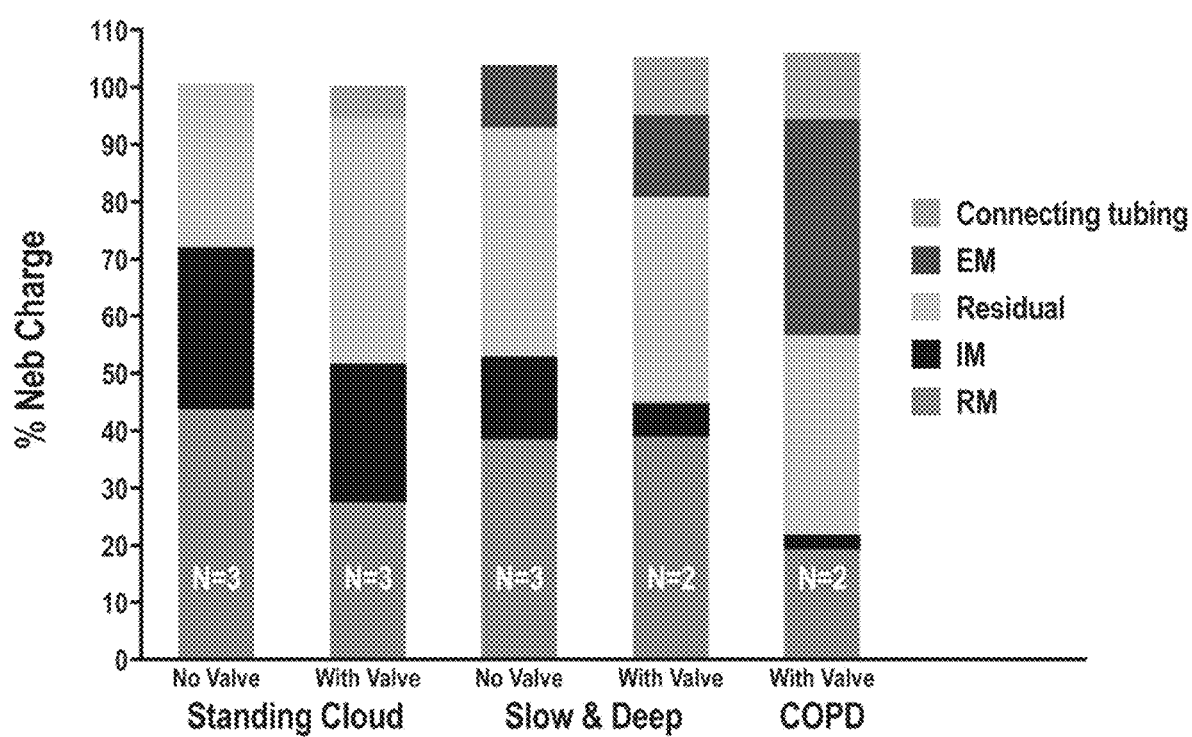
FIG. 27 is a bar graph showing the % Neb Charge for standing cloud and two breathing patterns: slow and deep breathing and COPD breathing using the set-up in FIG. 12A with saline aerosols labeled with $^{99m}TC$.
Figure 28:
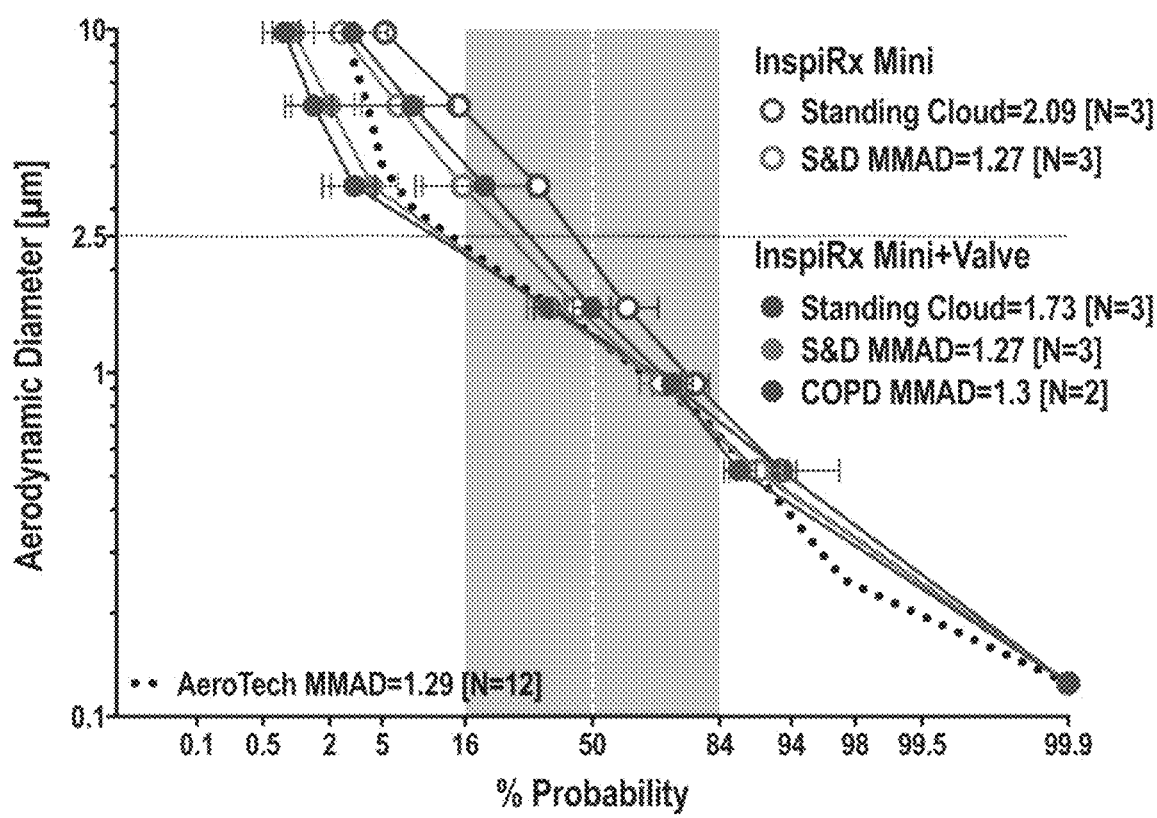
FIG. 28 is a plot showing the distribution of aerosol aerodynamic diameter for ventilated saline aerosols labeled with $^{99m}TC$ produced using the set-up of FIG. 12A using a breathing profile consistent with chronic obstructive pulmonary disease (COPD) slow and deep breathing and standing cloud.

FIG. 27 depicts the bar graph of the data tabulated hereinabove. In the bar graph, the connecting tubing refers to the aerosol mass deposited in the T connector 30 in FIG. 12A, EM refers to exhaled mass, IM refers to inhaled mass, RM refers to respirable mass and residual refers to unnebulized liquid mass. The data are also depicted in FIG. 28 as a log-log plot showing the distribution of aerosol aerodynamic diameter for aerosols produced using the apparatus of FIG. 12A As shown by the data in FIGS. 27 and 28, the InspiRx mini jet nebulizer, both with and without valve, utilizing its chamber design, delivers more drug than conventional devices with larger chambers, indicating a marked increase in efficiency. When ventilated with a slow and deep breathing pattern, the device produces an aerosol maximizing RM, predicting increase deep lung delivery with minimal upper airway distribution. Further, as shown by the data, the ventilated mini jet nebulizer described herein performed even better than the non-ventilated mini jet nebulizer of the present invention. As shown by the data, especially in Figure B, and based on comparison with the AeroTech™ nebulizer in which close to 99% of the particles that are inhaled reached the lungs. Based on these results, a significant portion, more than 90% would be predicted to reach the lungs for the unventilated mini nebulizer of the present invention, while greater than 99% of the inhaled particles are predicted to reach the lungs.

The above experiment was repeated, except that an interferon placebo formulation in solution (designated in the figures as "IFN Control Solution") was used. The interferon placebo formulation in solution contained the following ingredients: disodium succinate hexahydrate, 0.074% w/v; mannitol, 4.00% w/v; succinic acid, 0.028% w/v; polysorbate 80, 0.010% w/v; and the remainder water. In addition it was labeled with Technetium 99m radiolabel. This is also designated as the "IFN Control solution" or "IFN Control" and terms like "IFN Control", "IFN Control Solution" and "interferon placebo formulation in solution" are synonymous and are used interchangeably in the specification and in the figures.

Figure 29:
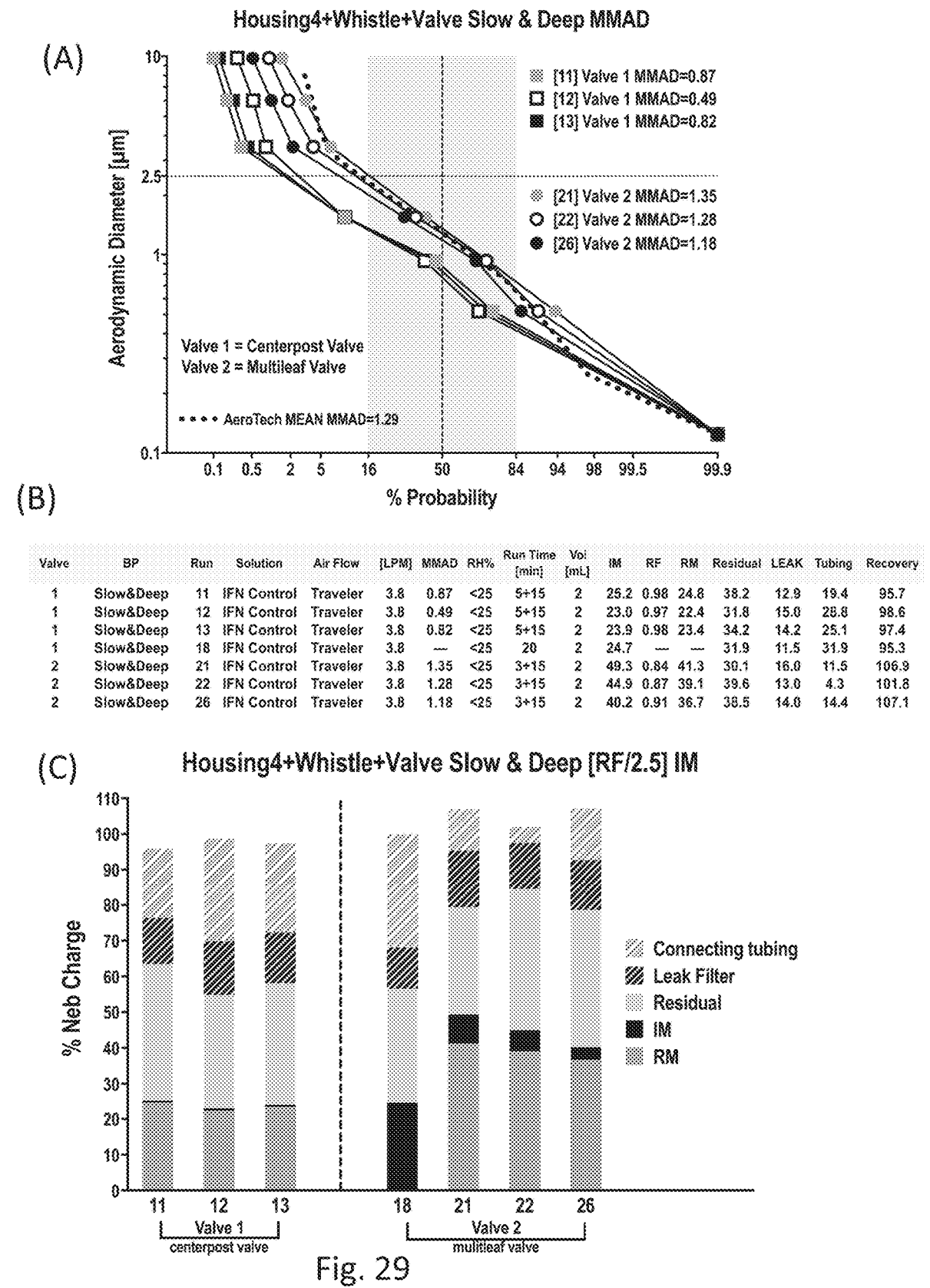
FIG. 29 provides data using the set-up of FIG. 12A using the nebulizer of the present invention having a centerpost valve or multileaf valve and whistle using a interferon placebo formulation in solution containing surfactant labeled with $^{99m}Tc$ using a breathing profile consistent with slow and deep breathing from runs 11-13 using a nebulizer of the present invention with one centerpost valve and whistle and runs 21, 22 and 26 using a nebulizer of the present invention with multi-leaf valve and whistle.

Only ventilated nebulizers were utilized, either having the centerpost valve or multileaf valve. The results are depicted in FIG. 29 (S&D conditions), FIG. 30 (S&D conditions) and FIG. 31 (COPD conditions). In these experiments, the AeroTech II® was used as a standard reference solely for purposes of particle distribution; it is not as efficient as the apparatus of the present invention.

The results indicate that the multi-leaf valve conditions the aerosol more efficiently than the center post valve producing a greater RM at a particle distribution identical to the AeroTech II® standard designed to maximize alveolar deposition. Again, the nebulizers performed well under the all three conditions. However, the use of the multileaf valve improved the efficiency of the nebulizer under all three conditions. For example, the presence of the multi-leaf valve increased the RM under slow and deep breathing conditions and COPD breathing conditions. Further, based on the data in the graphs, a greater amount of inhaled particles are predicted to reach the lungs using the nebulizer with multi-leaf valve and whistle than with the nebulizer with the centerpost valve and whistle. These data overcome the negative effects of the interferon placebo formulation in solution. The nebulizer is more efficient when nebulizing normal saline. When the formulation is changed to match that planned for interferon (e.g. a control solution of the formulation components without interferon, i.e., interferon placebo formulation in solution), nebulizer output is reduced compared to saline aerosols. The multi-leaf valve, overcomes this problem restoring efficiency to levels seen with saline.

As used herein, the singular forms "a," "an" and "the" include plural referents unless the context clearly dictates otherwise. Thus, for example, reference to a "valve" includes examples having two or more such "valves" unless the context clearly indicates otherwise. Furthermore, unless indicated to the contrary, the plural also denotes the singular.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that any particular order be inferred. Any recited single or multiple feature or aspect in any one claim can be combined or permuted with any other recited feature or aspect in any other claim or claims.

Moreover, unless indicated to the contrary, percentages are by weight.

It will be understood that when an element such as a layer, region or substrate is referred to as being formed on, deposited on, or disposed "on" or "over" another element, it can be directly on the other element or intervening elements may also be present. In contrast, when an element is referred to as being "directly on" or "directly over" another element, no intervening elements are present.

While various features, elements or steps of particular embodiments may be disclosed using the transitional phrase "comprising," it is to be understood that alternative embodiments, including those that may be described using the transitional phrases "consisting essentially of" or "consisting of" are implied. Thus, for example, implied alternative embodiments to a nebulizer that comprises a housing, a flue, and a cap include embodiments where a nebulizer consists essentially of a housing, a flue, and a cap, and embodiments where a nebulizer consists of a housing, a flue, and a cap.

Unless indicated to the contrary, reference to a range includes the endpoints as well as all of the values therebetween. Thus, for example, the range 0.5-1.0 includes the number 0.5 and 1.0 and all the values therebetween.

It will be apparent to those skilled in the art that various modifications and variations can be made to the present invention without departing from the spirit and scope of the invention. Since modifications, combinations, sub-combinations and variations of the disclosed embodiments incorporating the spirit and substance of the invention may occur to persons skilled in the art, the invention should be construed to include everything within the scope of the appended claims and their equivalents.

What is claimed is:

1. An apparatus for forming an aerosol comprising:
a main housing comprising a substantially cylindrical inner volume;
an axially-oriented gas inlet nozzle integral with the main housing and comprising a gas orifice at a distal end thereof;
an annular fluid reservoir disposed between an outer wall of the gas inlet nozzle and a sloped inner wall of the main housing;
a flue disposed within the inner volume, the flue comprising a sleeve portion slideably engaged with the gas inlet nozzle and defining an annular liquid flow passage therebetween, wherein an annular aerosol passage is disposed between an outer wall of the flue and an inner wall of the main housing;
primary baffle axially aligned with and spaced apart from the gas orifice;
a first secondary baffle extending radially from an outer surface of the flue through an arc in a plane perpendicular to a central axis of the flue and into the aerosol passage, the first secondary baffle comprising a substantially planar ledge forming a bottom surface thereof,
a second secondary baffle axially displaced from the first secondary baffle and extending radially from the outer surface of the flue through the same arc and into the aerosol passage, the second secondary baffle comprising an arcuate cross section having a bottom surface angled relative to the plane; and
a cap comprising a one-way inhalation valve, wherein the cap is sealably engaged with the main housing, wherein the one-way inhalation valve opens inwardly to allow ambient air to enter the main housing and closes to prevent aerosol from escaping the main housing.

2. The apparatus of claim 1, wherein an opening diameter of the gas orifice is 0.2 to 0.6 mm.

3. The apparatus of claim 1, wherein a width of the liquid flow passage is 0.1 to 0.5 mm.

4. The apparatus of claim 1, wherein a gap between a distal end of the sleeve portion and a bottom surface of the fluid reservoir is less than 2 mm.

5. The apparatus of claim 1, wherein a volume of the fluid reservoir is 0.5 to 2 ml.

6. The apparatus of claim 1, wherein the sloped inner wall is disposed at an angle of 10 to 40° with respect to a central axis of the main housing.

7. The apparatus of claim 1, wherein a distance between the gas orifice and the primary baffle is 0.2 to 1 mm.

8. The apparatus of claim 1, wherein a gap between each of the first secondary baffle and second secondary baffle and the inner wall of the housing, respectively, is 0.2 to 0.8 mm.

9. The apparatus of claim 1, further comprising a mouthpiece in fluid communication with an aerosol outlet extending through a sidewall of the main housing.

10. The apparatus of claim 9, wherein the mouthpiece comprises a one-way valve.

11. The apparatus of claim 9, further comprising a holding chamber disposed between the aerosol outlet and the mouthpiece.

12. The apparatus of claim 9, further comprising an inhalation orifice opening valve provided between and in fluid communication with the mouthpiece and the aerosol outlet, wherein the inhalation orifice opening valve is configured to adjust the size of aerosol particles passing through the inhalation orifice opening valve.

13. The apparatus of claim 12, wherein the inhalation orifice opening valve has one or more central openings.

14. The apparatus of claim 12, wherein the inhalation orifice opening valve has one or more side openings.

15. The apparatus of claim 12, further comprising an audible indicator provided to the cap of the apparatus, wherein the audible indicator is provided upstream of the one-way valve and configured to restrict an inlet air flow, thereby facilitating slow and deep breathing of a user.

16. The apparatus of claim 15, wherein the audible indicator comprises an opening of about 2 mm to about 4 mm.

17. The apparatus of claim 1, further comprising an audible indicator provided to the cap of the apparatus, wherein the audible indicator is provided upstream of the one-way valve and configured to restrict an inlet air flow, thereby facilitating slow and deep breathing of a user.

18. The apparatus of claim 17, wherein the audible indicator comprises an opening of about 2 mm to about 4 mm.

19. A method of forming an aerosol using the apparatus of claim 1, comprising adding an initial volume of 2 ml or less of a liquid drug or medicament to the liquid reservoir, and flowing gas through the gas inlet nozzle to form an aerosol of the liquid drug or medicament.

20. A method of forming an aerosol using the apparatus of claim 1, comprising flowing pressurized gas through the gas inlet nozzle at a flow rate of 1 to 10 liters per minute to form an aerosol from a liquid in the liquid reservoir.

21. The method of claim 20, wherein the pressurized gas flows through the gas inlet nozzle at a flow rate of 1 to 5 liters per minute.

22. A method of forming an aerosol using the apparatus of claim 1, comprising:
adding an initial volume of 2 ml or less of a liquid drug or medicament to the liquid reservoir; and
flowing pressurized gas through the gas inlet nozzle at a flow rate of 1 to 10 liters per minute to form an aerosol, wherein at least 50% of the initial volume is converted to an aerosol.

23. The method of claim 22, wherein the aerosol comprises a respiratory fraction (RF) of at least 70%.

24. The method of claim 22, wherein the aerosol comprises a respiratory fraction (RF) of at least 85%.

25. The method of claim 22, wherein the aerosol comprises a respirable mass (RM) of at least 20%.

26. The method of claim 22, wherein the aerosol comprises a respirable mass (RM) of at least 40%.

27. The method of claim 26, wherein the aerosol comprises a respirable mass (RM) of at least 50%.

28. The method of claim 22, further comprising inhaling the aerosol.

* * * * *